(12) United States Patent
Watanabe et al.

(10) Patent No.: US 7,687,222 B2
(45) Date of Patent: Mar. 30, 2010

(54) POLYMERIZABLE ESTER COMPOUNDS, POLYMERS, RESIST COMPOSITIONS AND PATTERNING PROCESS

(75) Inventors: Takeru Watanabe, Joetsu (JP); Takeshi Kinsho, Joetsu (JP); Koji Hasegawa, Joetsu (JP); Seiichiro Tachibana, Joetsu (JP); Masaki Ohashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 37 days.

(21) Appl. No.: 11/822,444

(22) Filed: Jul. 5, 2007

(65) Prior Publication Data

US 2008/0008962 A1    Jan. 10, 2008

(30) Foreign Application Priority Data

Jul. 6, 2006   (JP)   ............... 2006-186297

(51) Int. Cl.
G03F 7/039 (2006.01)
G03F 7/20 (2006.01)
G03F 7/30 (2006.01)
G03F 7/38 (2006.01)
C08F 20/10 (2006.01)

(52) U.S. Cl. .............. 430/270.1; 430/326; 430/325; 430/330; 560/205; 560/220; 526/328; 526/328.5; 526/329.4

(58) Field of Classification Search .............. None
See application file for complete search history.

(56) References Cited

U.S. PATENT DOCUMENTS

| 4,491,628 A | 1/1985 | Ito et al. |
| 5,310,619 A | 5/1994 | Crivello et al. |

(Continued)

FOREIGN PATENT DOCUMENTS

| JP | 63-27829 A | 2/1988 |
| JP | 2-27660 B2 | 6/1990 |

(Continued)

OTHER PUBLICATIONS

J. Photopolym. Sci. and Tech., vol. 8, No. 1, 1995, pp. 43-46.
J. Photopolym. Sci. and Tech., vol. 9, No. 1, 1996, pp. 29-30.

\* cited by examiner

*Primary Examiner*—Sin J. Lee
(74) *Attorney, Agent, or Firm*—Birch, Stewart, Kolasch & Birch, LLP

(57) ABSTRACT

Novel polymerizable ester compounds having formulae (1) to (4) undergo no acid-induced decomposition by β-elimination wherein $A^1$ is a polymerizable functional group having a carbon-carbon double bond, $R^1$ is H or $-C-(R^5)_3$, $R^2$ and $R^3$ are alkyl, $R^4$ is H or alkyl, $R^5$ is a monovalent hydrocarbon group, X is alkylene, Y is methylene, ethylene or isopropylidene, Z is alkylene, and n=1 or 2. Resist compositions comprising polymers derived from the ester compounds have excellent sensitivity and resolution and lend themselves to micropatterning lithography.

(1)

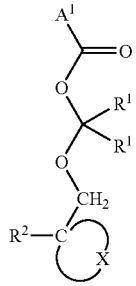

(2)

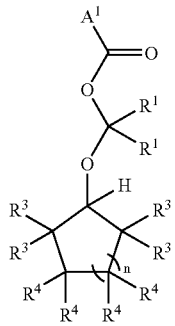

(3)

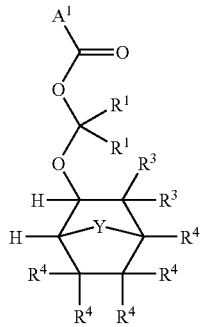

(4)

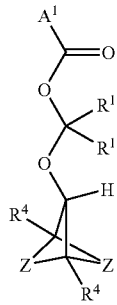

9 Claims, No Drawings

U.S. PATENT DOCUMENTS

| | | |
|---|---|---|
| 5,714,625 A | 2/1998 | Hada et al. |
| 6,004,724 A | 12/1999 | Yamato et al. |
| 6,063,953 A | 5/2000 | Hada et al. |
| 6,200,725 B1 | 3/2001 | Takechi et al. |
| 6,261,738 B1 | 7/2001 | Asakura et al. |
| 6,280,898 B1 | 8/2001 | Hasegawa et al. |
| 6,312,867 B1 | 11/2001 | Kinsho et al. |
| 6,329,125 B2 | 12/2001 | Takechi et al. |
| 6,448,420 B1 | 9/2002 | Kinsho et al. |
| 6,916,591 B2 | 7/2005 | Ohsawa et al. |
| 7,186,495 B2 | 3/2007 | Maeda et al. |
| 2008/0096126 A1* | 4/2008 | Kinoshita et al. ........ 430/270.1 |
| 2008/0193871 A1* | 8/2008 | Ogata et al. .............. 430/270.1 |

FOREIGN PATENT DOCUMENTS

| | | |
|---|---|---|
| JP | 9-73173 A | 3/1997 |
| JP | 9-90637 A | 4/1997 |
| JP | 9-95479 A | 4/1997 |
| JP | 9-208554 A | 8/1997 |
| JP | 9-230588 A | 9/1997 |
| JP | 9-230595 A | 9/1997 |
| JP | 9-301948 A | 11/1997 |
| JP | 10-10739 A | 1/1998 |
| JP | 2906999 B2 | 4/1999 |
| JP | 2000-26446 A | 1/2000 |
| JP | 2000-159758 A | 6/2000 |
| JP | 2000-314956 A | 11/2000 |
| JP | 2000-327633 A | 11/2000 |
| JP | 2000-336121 A | 12/2000 |
| WO | WO-97/33198 A1 | 9/1997 |
| WO | WO 2005/123795 A1 * | 12/2005 |
| WO | WO 2006/040949 A1 * | 4/2006 |

POLYMERIZABLE ESTER COMPOUNDS, POLYMERS, RESIST COMPOSITIONS AND PATTERNING PROCESS

CROSS-REFERENCE TO RELATED APPLICATION

This non-provisional application claims priority under 35 U.S.C. §119(a) on Patent Application No. 2006-186297 filed in Japan on Jul. 6, 2006, the entire contents of which are hereby incorporated by reference.

TECHNICAL FIELD

This invention relates to (1) a novel polymerizable acid-labile ester compound having a specific structure, (2) a polymer comprising units derived from the ester compound which is blended as a base resin to formulate a resist composition suitable in the micropatterning technology, (3) a chemically amplified positive resist composition comprising the polymer, and (4) a patterning process using the resist composition.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. In particular, the change-over from i-line (365 nm) to shorter wavelength KrF laser (248 nm) brought about a significant innovation, enabling mass-scale production of 0.18 micron rule devices. To the demand for a resist material with a higher resolution and sensitivity, acid-catalyzed chemical amplification positive working resist materials are effective as disclosed in U.S. Pat. No. 4,491,628 and U.S. Pat. No. 5,310,619 (JP-B 2-27660 and JP-A 63-27829). They now become predominant resist materials especially adapted for deep UV lithography.

Resist materials adapted for KrF excimer lasers enjoyed early use on the 0.3 micron process, passed through the 0.25 micron rule, and currently entered the mass production phase on the 0.18 micron rule. Engineers have started investigation on the 0.15 micron rule, with the trend toward a finer pattern rule being accelerated. A wavelength change-over from KrF to shorter wavelength ArF laser (193 nm) is expected to enable miniaturization of the design rule to 0.13 μm or less. Since conventionally used novolac resins and polyvinylphenol resins have very strong absorption in proximity to 193 nm, they are difficult to use as the base resin for resists. To ensure transparency and dry etching resistance, some engineers investigated acrylic and cycloolefin resins as disclosed in JP-A 9-73173, JP-A 10-10739, JP-A 9-230595 and WO 97/33198.

Among others, a focus is drawn on (meth)acrylic resin base resists featuring a high resolution. One of the (meth)acrylic resins proposed thus far is a combination of (meth)acrylic units having methyladamantane ester as acid labile group units with (meth)acrylic units having lactone ring ester as adhesive group units as disclosed in JP-A. 9-90637. Acid labile groups of exo form are described in U.S. Pat. No. 6,448,420 (JP-A 2000-327633). These groups have so high an acid elimination ability and require a low level of activation energy for acid elimination, affording a high resolution and low dependence on post-exposure bake (PEB). Norbornane lactone is also proposed as an adhesive group having enhanced etching resistance as disclosed in JP-A 2000-26446 and JP-A 2000-159758. These studies have achieved significant improvements in the resolution of ArF resists.

The outstanding problem associated with the ArF lithography for forming a fine feature pattern is to meet both a high resolution and a minimized size difference between isolated and grouped patterns (known as I/G bias or proximity bias). So far as either one of high resolution and improved I/G bias is concerned, prior art techniques can achieve the goal to some extent. However, it is very difficult to meet both the requirements at a high level.

In general, resins for ArF resists have a structure in which carboxyl groups serving as the alkali soluble group are protected with acid labile groups, and perform such that the acid labile group is deprotected under the action of an acid to regenerate carboxyl groups whereby the resins become soluble in alkaline developers. It is noted that deprotection under the action of an acid is referred to as acid decomposition or "acidolysis." A choice of an acid labile group having higher reactivity may be advantageous with respect to resolution, but enhance acid diffusion during acidolysis reaction, tending to degrade I/G bias. It is thus difficult to meet both resolution and I/G bias at a high level.

DISCLOSURE OF THE INVENTION

An object of the invention is to provide a chemically amplified positive resist composition which is used to form a fine feature pattern while satisfying high levels of resolution and I/G bias and is thus suited as a micropatterning material in the manufacture of VLSI or photomask patterns; a polymer which is compounded as a base resin to formulate the resist composition; a polymerizable ester compound from which the polymer is formed; and a patterning process using the resist composition.

It has been found that acid-labile ester compounds having a specific structure can be prepared by a method to be described later; and that when polymers comprising units derived from the acid-labile ester compounds are compounded as a base resin, the resulting resist compositions can satisfy both excellent resolution and improved I/G bias with regard to both line-and-space patterns and contact-hole patterns.

Accordingly, the present invention provides a novel polymerizable acid-labile ester compound of specific structure, a polymer derived from the ester compound and useful as a base resin in resist materials for lithographic micropatterning, a chemically amplified positive resist composition comprising the polymer, and a patterning process.

In a first aspect, the invention provides a polymerizable acid-labile ester compound having a structure that undergoes no acid-induced decomposition by beta-elimination, and represented by any one of the following general formulae (1) to (4):

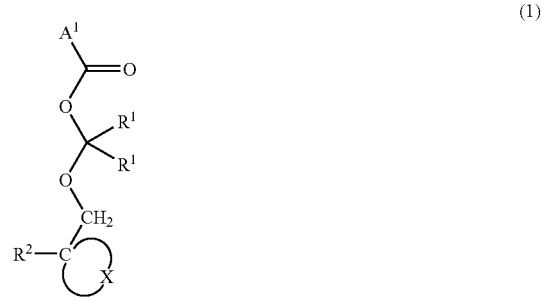

(1)

-continued (2)
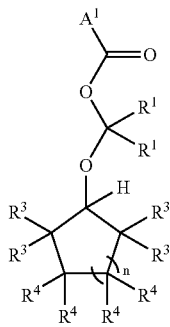

(3)
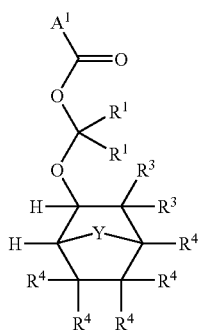

(4)
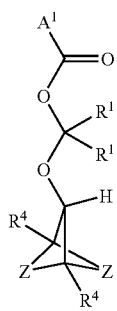

wherein $A^1$ is a polymerizable functional group having a carbon-carbon double bond, $R^1$ is each independently hydrogen or —C—$(R^5)_3$, $R^2$ is a straight, branched or cyclic $C_1$-$C_{10}$ alkyl group, $R^3$ is each independently a straight, branched or cyclic $C_1$-$C_{10}$ alkyl group, $R^4$ is each independently hydrogen or a straight, branched or cyclic $C_1$-$C_{10}$ alkyl group, or a combination of $R^3$, a combination of $R^4$, or a combination of $R^3$ and $R^4$ may bond together to form an aliphatic hydrocarbon ring with some carbon atoms in the ring to which they are attached, and in that event, each of $R^3$ and $R^4$ is a straight, branched or cyclic $C_1$-$C_{10}$ alkylene group, $R^5$ is each independently a straight, branched or cyclic monovalent hydrocarbon group of 1 to 10 carbon atoms, or a combination of $R^5$ may bond together to form an aliphatic hydrocarbon ring with the carbon atom to which they are attached, and in that event, $R^5$ is a straight, branched or cyclic $C_2$-$C_{10}$ alkylene group, X is a straight, branched or cyclic $C_2$-$C_{20}$ alkylene group which forms an aliphatic hydrocarbon ring with the carbon atom to which it is attached at both ends, Y is a methylene, ethylene or isopropylidene group, Z is each independently a straight, branched or cyclic $C_1$-$C_{10}$ alkylene group which forms a 4- to 7-membered ring with the three-carbon chain to which it is attached at both ends, and n is 1 or 2, with the proviso that $R^1$ to $R^5$, X, Y, and Z are free of heteroatoms other than carbon and hydrogen atoms.

Preferred are ester compounds having the general formula (5):

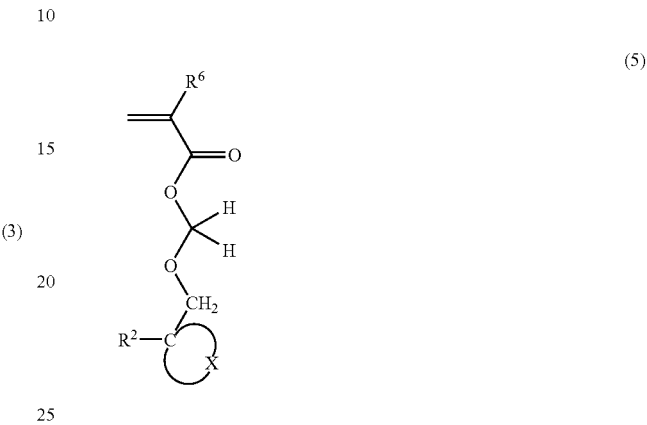

wherein $R^2$ is a straight, branched or cyclic $C_1$-$C_{10}$ alkyl group, $R^6$ is hydrogen, methyl or trifluoromethyl, and X is a straight, branched or cyclic $C_2$-$C_{20}$ alkylene group which forms an aliphatic hydrocarbon ring with the carbon atom to which it is attached at both ends, with the proviso that $R^2$ and X are free of heteroatoms other than carbon and hydrogen atoms.

Preferred are ester compounds having the general formula (6):

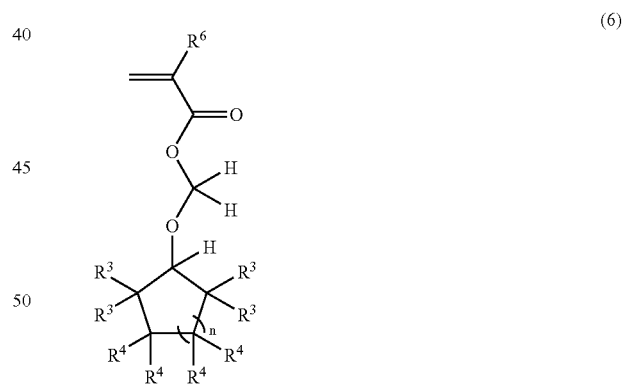

wherein $R^3$ is each independently a straight, branched or cyclic $C_1$-$C_{10}$ alkyl group, $R^4$ is each independently hydrogen or a straight, branched or cyclic $C_1$-$C_{10}$ alkyl group, or a combination of $R^3$, a combination of $R^4$, or a combination of $R^3$ and $R^4$ may bond together to form an aliphatic hydrocarbon ring with some carbon atoms in the ring to which they are attached, and in that event, each of $R^3$ and $R^4$ is a straight, branched or cyclic $C_1$-$C_{10}$ alkylene group, $R^6$ is hydrogen, methyl or trifluoromethyl, and n is 1 or 2, with the proviso that $R^3$ and $R^4$ are free of heteroatoms other than carbon and hydrogen atoms.

Preferred are ester compounds having the general formula (7):

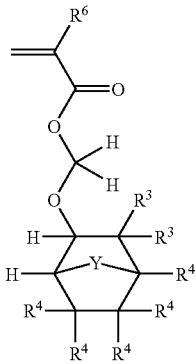

(7)

wherein $R^3$ is each independently a straight, branched or cyclic $C_1$-$C_{10}$ alkyl group, $R^4$ is each independently hydrogen or a straight, branched or cyclic $C_1$-$C_{10}$ alkyl group, or a combination of $R^3$, a combination of $R^4$, or a combination of $R^3$ and $R^4$ may bond together to form an aliphatic hydrocarbon ring with some carbon atoms in the ring to which they are attached, and in that event, each of $R^3$ and $R^4$ is a straight, branched or cyclic $C_1$-$C_{10}$ alkylene group, $R^6$ is hydrogen, methyl or trifluoromethyl, and Y is a methylene, ethylene or isopropylidene group, with the proviso that $R^3$, $R^4$ and Y are free of heteroatoms other than carbon and hydrogen atoms.

Preferred are ester compounds having the general formula (8):

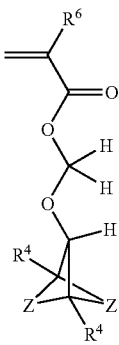

(8)

wherein $R^4$ is each independently hydrogen or a straight, branched or cyclic $C_1$-$C_{10}$ alkyl group, or a combination of $R^4$ may bond together to form an aliphatic hydrocarbon ring with some carbon atoms in the ring to which it is attached, and in that event, each of $R^4$ is a straight, branched or cyclic $C_1$-$C_{10}$ alkylene group, $R^6$ is hydrogen, methyl or trifluoromethyl, and Z is each independently a straight, branched or cyclic $C_1$-$C_{10}$ alkylene group which forms a 4- to 7-membered ring with the three-carbon chain to which it is attached at both ends, with the proviso that $R^4$ and Z are free of heteroatoms other than carbon and hydrogen atoms.

In a second aspect, the invention provides a polymer comprising at least recurring units derived from one or more polymerizable acid-labile ester compounds of formulae (1) to (8) and having a weight average molecular weight of 2,000 to 100,000.

The polymer may further comprise recurring units of at least one type selected from the following general formula (R1).

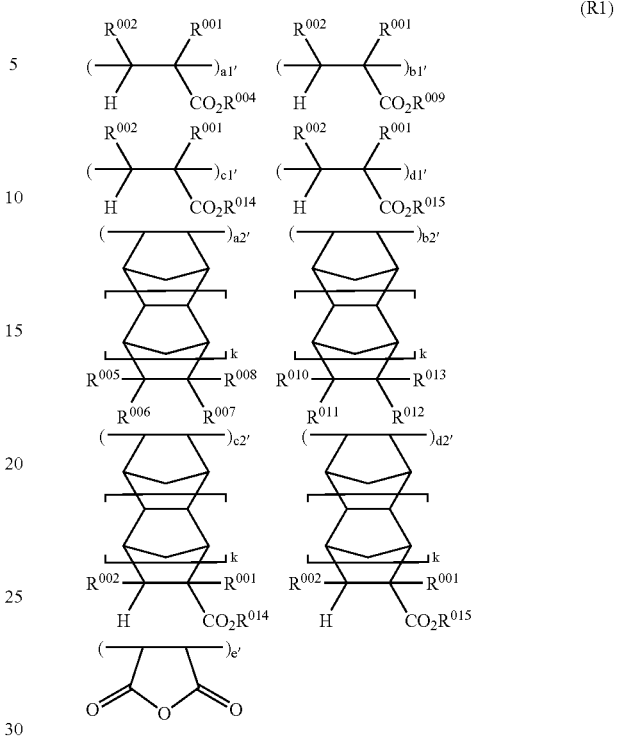

(R1)

Herein $R^{001}$ is hydrogen, fluorine, methyl, trifluoromethyl or $CH_2CO_2R^{003}$; $R^{002}$ is hydrogen, methyl or $CO_2R^{003}$; $R^{003}$ is a straight, branched or cyclic $C_1$-$C_{15}$ alkyl group; $R^{004}$ is hydrogen or a monovalent hydrocarbon group of 1 to 15 carbon atoms having at least one group selected from among fluorinated substituent groups, carboxyl, hydroxyl and cyano groups; at least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups, or a combination of $R^{005}$ to $R^{008}$ may bond together to form a ring, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to $R^{008}$ are each independently single bonds, hydrogen atoms or straight, branched or cyclic $C_1$-$C_{15}$ alkyl groups; $R^{009}$ is a monovalent hydrocarbon group of 3 to 15 carbon atoms containing a —$CO_2$— partial structure; at least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups, or a combination of $R^{010}$ to $R^{013}$ may bond together to form a ring, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups; $R^{014}$ is a polycyclic hydrocarbon group having 7 to 15 carbon atoms or an alkyl group containing such a polycyclic hydrocarbon group; $R^{015}$ is an acid labile group; a1', a2', b1', b2', c1', c2', d1', d2', and e' indicative of ratios of corresponding recurring units to the total recurring units in the polymer are numbers from 0 to less than 1; and k is 0 or 1.

The preferred polymer may comprise recurring units derived from the polymerizable acid-labile ester compound of any one of formulae (1) to (8) in a molar fraction of 5% to 70%.

In a third aspect, the invention provides a resist composition comprising the polymer defined above; a resist composition comprising (A) the polymer defined above, (B) an acid generator, and (C) an organic solvent; a resist composition comprising (A) the polymer defined above, (B) an acid generator, (C) an organic solvent, and (D) a sensitivity regulator; or a resist composition comprising (A) the polymer defined above, (B) an acid generator, (C) an organic solvent, (D) a sensitivity regulator, and (E) a surfactant.

In a fourth aspect, the invention provides a process for forming a pattern, comprising the steps of applying the resist composition onto a substrate to form a resist coating; heat treating the coating and exposing to high-energy radiation or electron beam through a photomask; and heat treating the exposed coating and developing with a developer.

It is noted that immersion lithography can be applied to the resist composition of the invention. The immersion lithography involves prebaking a resist film and exposing the resist film to light through a projection lens with a liquid medium interposed between the resist film and the projection lens. The ArF immersion lithography uses deionized water as the immersion medium. This technology, combined with a projection lens having a numerical aperture of at least 1.0, is important for the ArF lithography to survive to the 65 nm node, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when the inventive polymer is blended with a hydrogenated cycloolefin ring-opening metathesis polymer (ROMP) having a low Tg.

BENEFITS OF THE INVENTION

A resist composition comprising a polymer resulting from the ester compound of the invention as a base resin has a high sensitivity and resolution, and satisfies both excellent resolution and improved I/G bias. It is suited as a micropatterning material in the manufacture of VLSI and analogous elements.

DESCRIPTION OF THE PREFERRED EMBODIMENT

The singular forms "a," "an" and "the" include plural referents unless the context clearly dictates otherwise.

The notation (Cn-Cm) means a group containing from n to m carbon atoms per group.

It is understood that for many structures represented by chemical formulae, there can exist enantiomers and diastereomers. Unless otherwise stated, a single formula collectively represents all such stereoisomers. The stereoisomers may be used alone or in admixture.

Ester Compound

The polymerizable acid-labile ester compounds of the invention have a structure that undergoes no acid-induced decomposition by beta-elimination, and represented by the following general formulae (1) to (4).

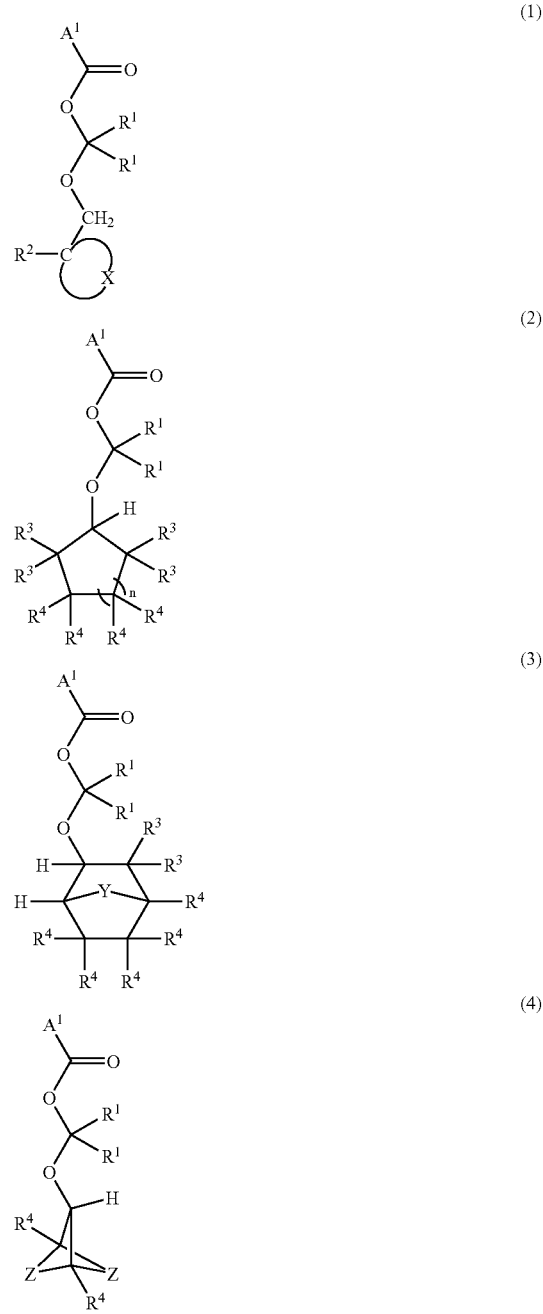

Herein $A^1$ is a polymerizable functional group having a carbon-carbon double bond. $R^1$ is each independently hydrogen or —C—$(R^5)_3$. $R^2$ is a straight, branched or cyclic $C_1$-$C_{10}$ alkyl group. $R^3$ is each independently a straight, branched or cyclic $C_1$-$C_{10}$ alkyl group. $R^4$ is each independently hydrogen or a straight, branched or cyclic $C_1$-$C_{10}$ alkyl group. Alternatively, a combination of $R^3$, a combination of $R^4$, or a combination of $R^3$ and $R^4$ may bond together to form an aliphatic hydrocarbon ring with some carbon atoms in the ring to which they are attached, and in that event, each of $R^3$ and $R^4$ is a straight, branched or cyclic $C_1$-$C_{10}$ alkylene group. $R^5$ is each independently a straight, branched or cyclic monovalent hydrocarbon group of 1 to 10 carbon atoms. Alternatively, a combination of $R^5$ may bond together to form an aliphatic hydrocarbon ring with the carbon atom to which they are attached, and in that event, $R^5$ is a straight, branched or cyclic $C_2$-$C_{10}$ alkylene group. X is a straight, branched or cyclic $C_2$-$C_{20}$ alkylene group which forms an aliphatic hydrocarbon ring with the carbon atom to which it is attached at both ends. Y is a methylene, ethylene or isopropylidene group. Z is each independently a straight, branched or cyclic $C_1$-$C_{10}$ alkylene group which forms a 4- to 7-membered ring with the three-carbon chain to which it is attached at both ends, and n is 1 or 2. $R^1$ to $R^5$, X, Y, and Z are free of heteroatoms other than carbon and hydrogen atoms.

In the prior art, ArF resist resins use acid labile protective groups for carboxylic acid which include tertiary alkyl groups such as 2-methyl-2-adamantyl and acetal groups such as 1-ethoxyethyl and cyclohexyloxymethyl. As shown in the following schema, these groups have at least one beta-hydrogen and allow for acid-induced decomposition or deprotection by a beta-elimination mechanism. Mainly the following routes of decomposition are anticipated. In this disclosure, a carbon atom attached to an oxygen atom is designated α-carbon, a carbon atom at a vicinal position to α-carbon is designated β-carbon, a hydrogen atom on β-carbon is designated β-hydrogen, and the term "β-elimination" as used herein means that deprotection occurs as a result of β-hydrogen being eliminated.

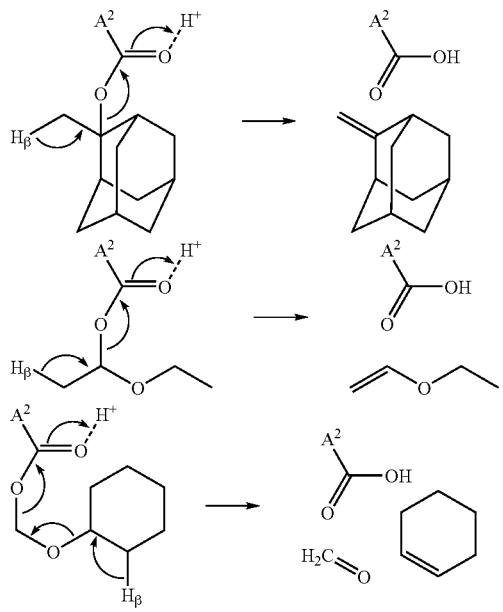

Herein, $A^2$ is a monovalent group attached to the polymer backbone.

In contrast are the polymerizable acid-labile ester compounds of the invention. In formulae (1) and (2), β-hydrogen atoms which would participate in elimination are not present at all. In formulae (3) and (4), β-hydrogen atoms may be present, but the special bicyclo ring structure makes it impossible to form a double bond by β-elimination because of Bredt rule unless the carbon skeleton is altered by rearrangement reaction. For the structural reason, it never happens in theory that the compounds of formulae (1) to (4) undergo acid-induced decomposition by β-elimination.

This suggests that the mechanism of deprotection reaction of acid labile group which is a key chemical reaction dictating the resolution of chemically amplified positive resists differs significantly between the prior art resist compositions and the inventive resist compositions. It is this difference that contributes toward satisfying both high resolution and improved I/G bias, which has been difficult to achieve with the existing resist compositions.

In general formulae (1) to (4), $A^1$ is a polymerizable functional group having a carbon-carbon double bond. It is preferably selected from the groups shown below, but not limited thereto. Note that the broken line indicates a bonding site.

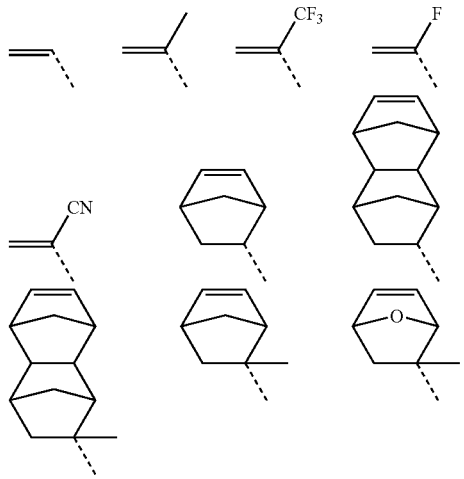

$R^1$ is each independently a hydrogen atom or $-C-(R^5)_3$. $R^5$ is each independently a straight, branched or cyclic monovalent hydrocarbon group of 1 to 10 carbon atoms. Alternatively, a combination of $R^5$ may bond together to form an aliphatic hydrocarbon ring with the carbon atom to which they are attached, and in that event, $R^5$ is a straight, branched or cyclic $C_2$-$C_{10}$ alkylene group. $R^5$ does not contain heteroatoms other than carbon and hydrogen atoms. Where $R^1$ is $-C-(R^5)_3$, illustrative examples include, but are not limited to, t-butyl, t-amyl, 1-methylcyclohexyl, and 1-adamantyl. Preferably $R^1$ is hydrogen.

$R^2$ is a straight, branched or cyclic $C_1$-$C_{10}$ alkyl group. It does not contain heteroatoms other than carbon and hydrogen atoms. Examples include, but are not limited to, methyl, ethyl, propyl, isopropyl, butyl, sec-butyl, tert-butyl, tert-amyl, pentyl, hexyl, cyclopentyl, cyclohexyl, norbornyl, and adamantyl. Preferably $R^2$ is methyl or ethyl.

$R^3$ is each independently a straight, branched or cyclic $C_1$-$C_{10}$ alkyl group while it is not hydrogen. $R^4$ is each independently hydrogen or a straight, branched or cyclic $C_1$-$C_{10}$ alkyl group. Alternatively, a combination of $R^3$, a combination of $R^4$, or a combination of $R^3$ and $R^4$ may bond together to form an aliphatic hydrocarbon ring with some carbon atoms in the ring to which they are attached, and in that event, each of $R^3$ and $R^4$ is a straight, branched or cyclic $C_1$-$C_{10}$ alkylene group. $R^3$ and $R^4$ do not contain heteroatoms other than carbon and hydrogen atoms.

Examples of the straight, branched or cyclic $C_1$-$C_{10}$ alkyl group represented by $R^3$ and $R^4$ include, but are not limited to, methyl, ethyl, propyl, isopropyl, butyl, sec-butyl, tert-butyl, tert-amyl, pentyl, hexyl, cyclopentyl, cyclohexyl, norbornyl, and adamantyl. In the event that a combination of $R^3$, a combination of $R^4$, or a combination of $R^3$ and $R^4$ bond together to form an aliphatic hydrocarbon ring with some carbon atoms in the ring to which they are attached, examples of the aliphatic hydrocarbon ring include, but are not limited to, cyclopropane, cyclobutane, cyclopentane, cyclohexane, cycloheptane, bicyclo[3.3.0]ocatane, and tricyclo[5.2.1.0$^{2,6}$] decane rings and alkyl-substituted forms of these rings.

In formula (1), X is a straight, branched or cyclic $C_2$-$C_{20}$ alkylene group which forms an aliphatic hydrocarbon ring with the carbon atom to which it is attached at both ends. It does not contain heteroatoms other than carbon and hydrogen atoms. Examples of the aliphatic hydrocarbon ring that X forms with the carbon atom to which it is attached at both ends, that is, of the general formula (9):

(9)

include, but are not limited to, cyclopropane, cyclobutane, cyclopentane, cyclohexane, cycloheptane, norbornane, bicyclo[3.3.0]octatane, bicyclo[2.2.2]octane, tricyclo[5.2.1.0$^{2,6}$] decane, adamantane, decahydronaphthalene, octahydroindene, tetracyclo[6.2.1.1$^{3,6}$.0$^{2,7}$]dodecane rings and alkyl-substituted forms of these rings.

In formula (3), Y is a methylene, ethylene or isopropylidene group, and preferably methylene.

In formula (4), Z is each independently a straight, branched or cyclic $C_1$-$C_{10}$ alkylene group which forms a 4- to 7-membered ring with the three-carbon chain to which it is attached at both ends. It does not contain heteroatoms other than carbon and hydrogen atoms. Examples of the 4- to 7-membered ring that Z forms with the three-carbon chain to which it is attached at both ends, that is, the partial structure of the general formula (10):

(10)

within formula (4) include cyclobutane, cyclopentane, cyclohexane, cycloheptane rings and alkyl-substituted forms of these rings.

The subscript n is 1 or 2.

It is noted that where the polymerizable acid-labile ester compounds of formulae (1) to (4) are applied to ArF resists, it is desirable from the standpoint of light absorption at the wavelength 193 nm of the ArF excimer laser that none of $R^1$ to $R^5$, X, Y, and Z have a double bond.

All the polymerizable acid-labile ester compounds of formulae (1) to (4) have an alicyclic structure, which contributes to an improvement in the etch resistance of resist compositions of the invention.

Examples of the polymerizable acid-labile ester compound of formula (1) include, but are not limited to, those compounds illustrated below, in addition to examples of the polymerizable acid-labile ester compound of formula (5) which will be illustrated later.

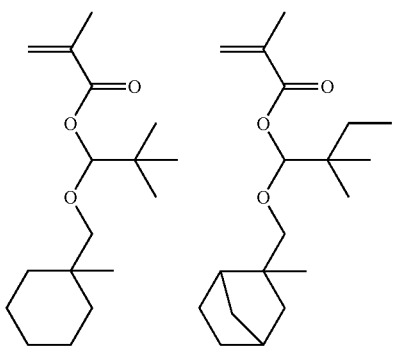

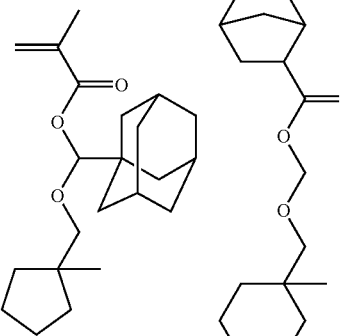

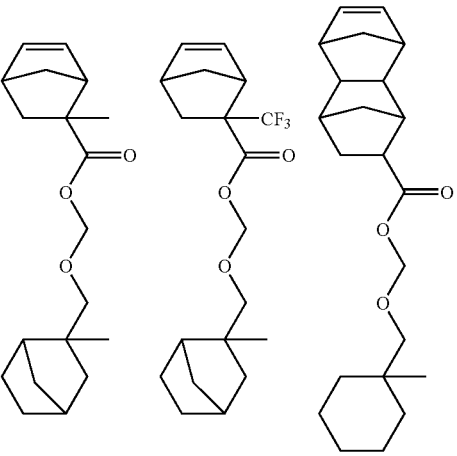

Examples of the polymerizable acid-labile ester compound of formula (2) include, but are not limited to, those compounds illustrated below, in addition to examples of the polymerizable acid-labile ester compound of formula (6) which will be illustrated later.

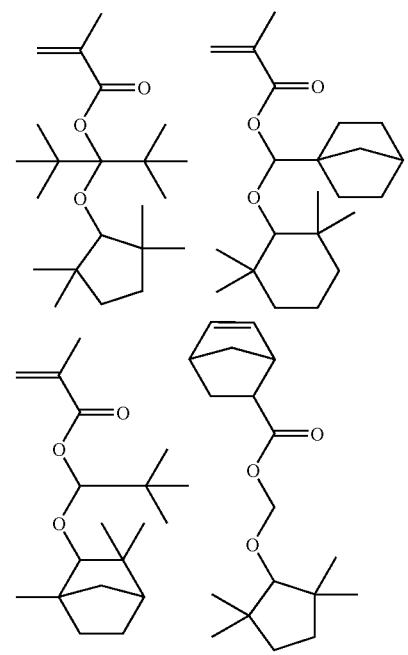

-continued

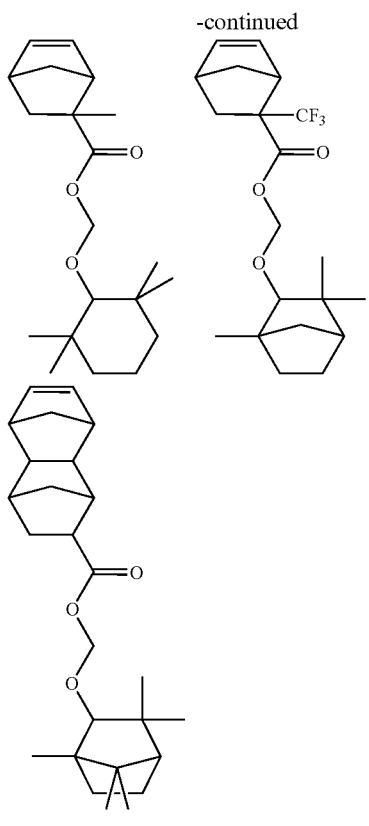

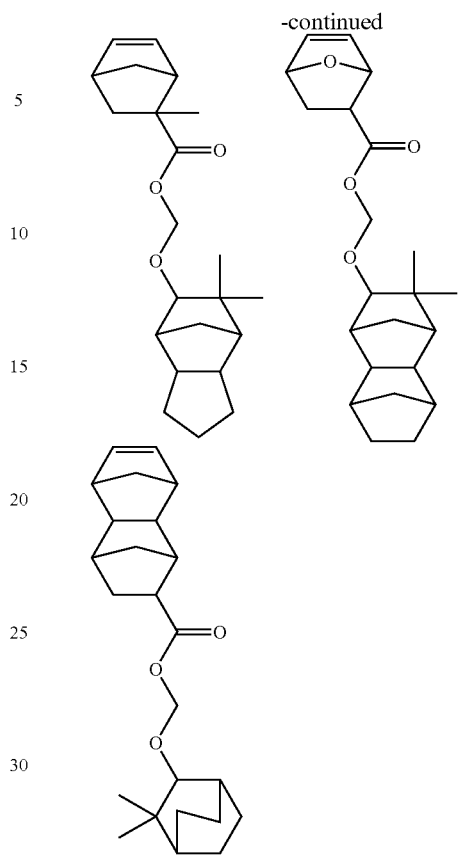

Examples of the polymerizable acid-labile ester compound of formula (3) include, but are not limited to, those compounds illustrated below, in addition to examples of the polymerizable acid-labile ester compound of formula (7) which will be illustrated later.

Examples of the polymerizable acid-labile ester compound of formula (4) include, but are not limited to, those compounds illustrated below, in addition to examples of the polymerizable acid-labile ester compound of formula (8) which will be illustrated later.

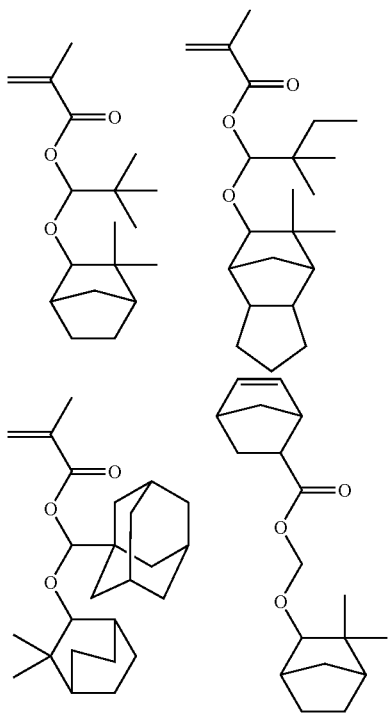

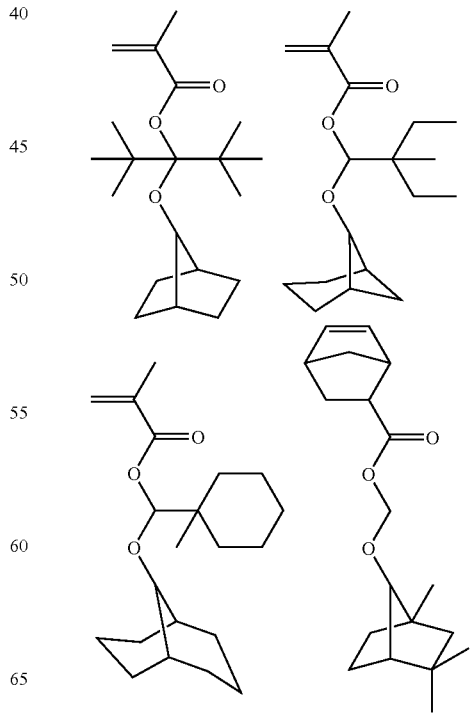

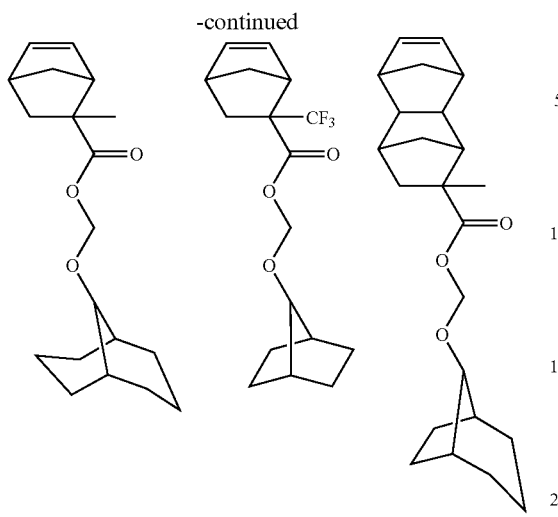

Of the polymerizable acid-labile ester compounds having formulae (1) to (4), those having the following general formulae (5) to (8) are preferred.

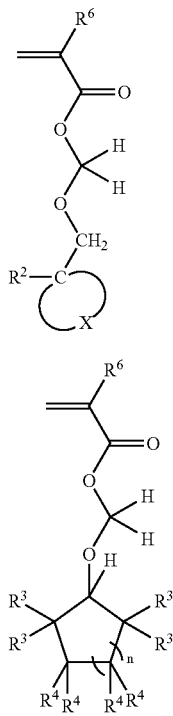

(5)

(6)

(7)

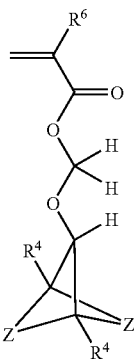

(8)

Herein $R^2$ to $R^4$, X, Y, Z and n are as defined above, and $R^6$ is a hydrogen atom, methyl group or trifluoromethyl group.

Now that $R^6$ is hydrogen, methyl or trifluoromethyl, the polymerizable acid-labile ester compounds having formulae (5) to (8) are given a high radical polymerization capability, so that a variety of polymers can be prepared therefrom which are useful as the base resin in a variety of resist compositions best suited in many applications.

Examples of the polymerizable acid-labile ester compound of formula (5) include, but are not limited to, those compounds illustrated below.

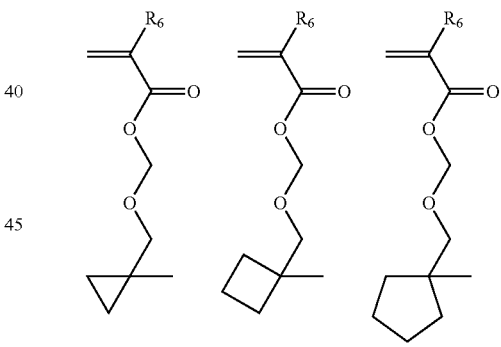

-continued
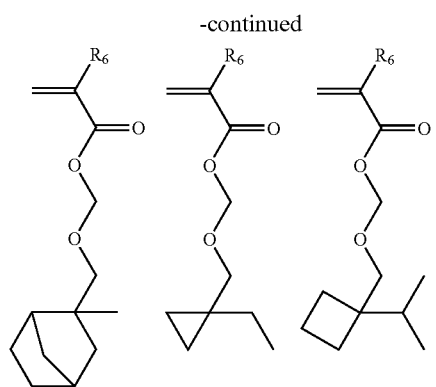
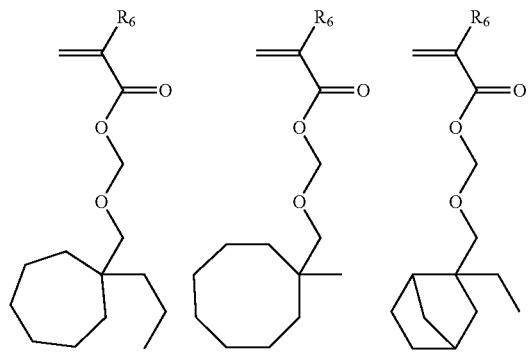
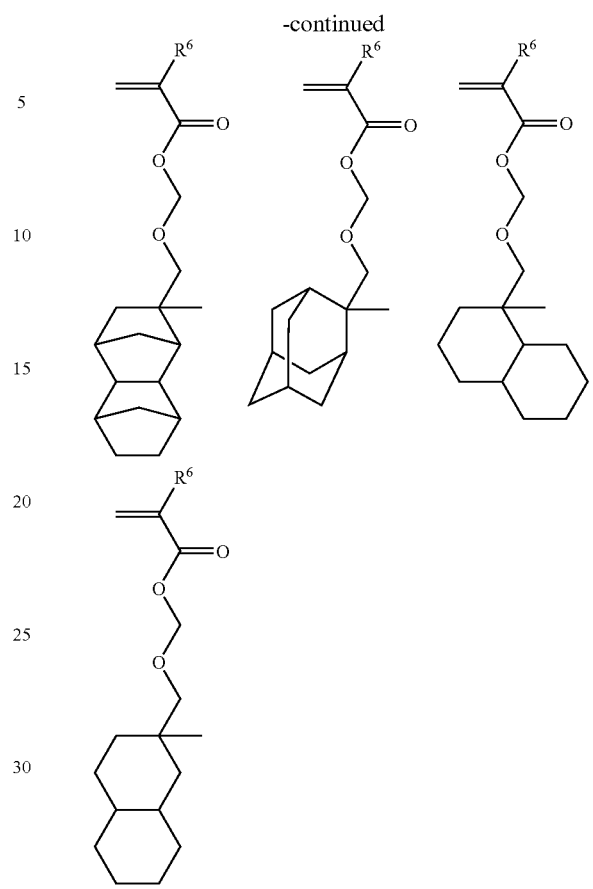
Herein $R^6$ is hydrogen, methyl or trifluoromethyl.
Examples of the polymerizable acid-labile ester compound of formula (6) include, but are not limited to, those compounds illustrated below.
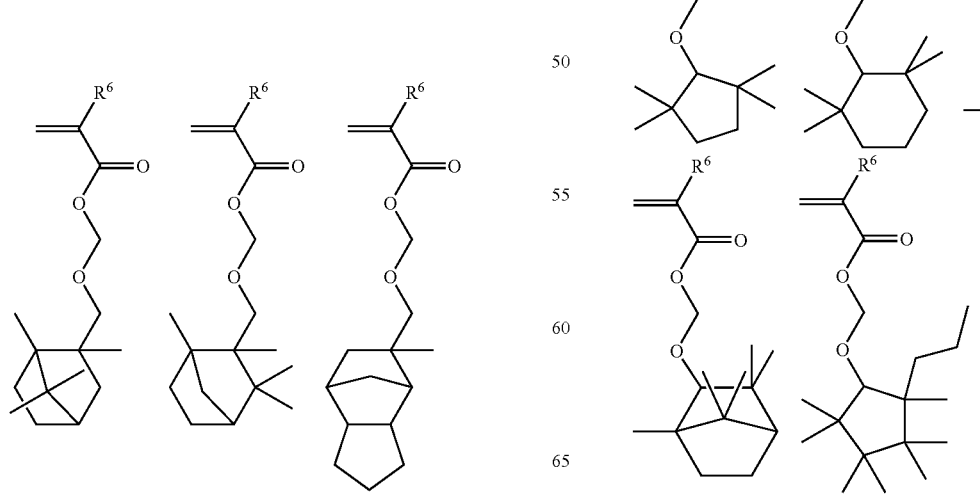

-continued

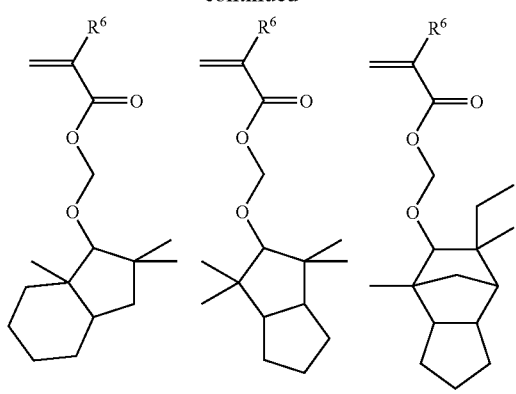

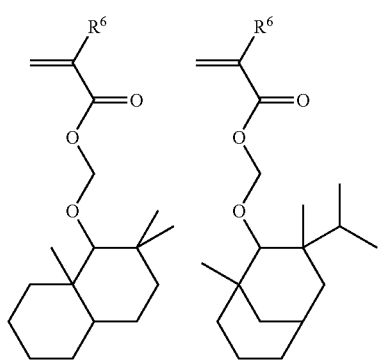

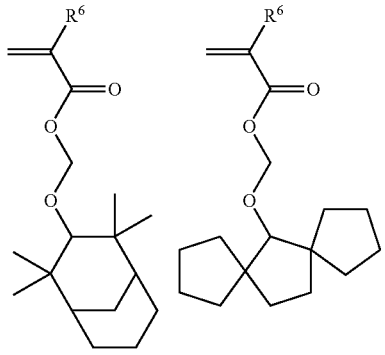

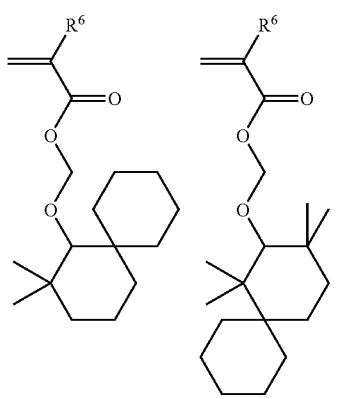

Herein R⁶ is hydrogen, methyl or trifluoromethyl.

Examples of the polymerizable acid-labile ester compound of formula (7) include, but are not limited to, those compounds illustrated below.

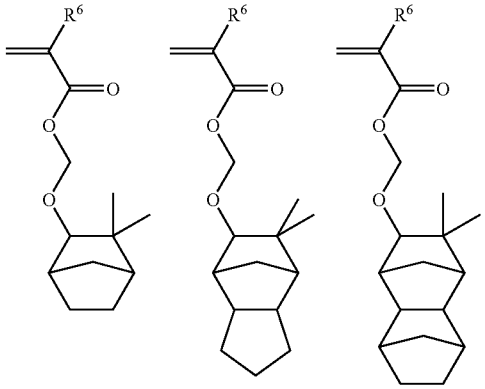

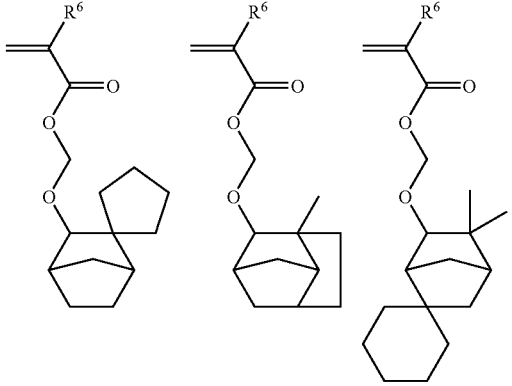

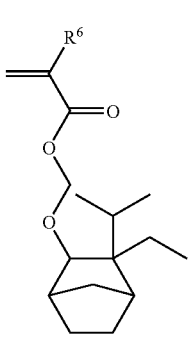

Herein R⁶ is hydrogen, methyl or trifluoromethyl.

Examples of the polymerizable acid-labile ester compound of formula (8) include, but are not limited to, those compounds illustrated below.

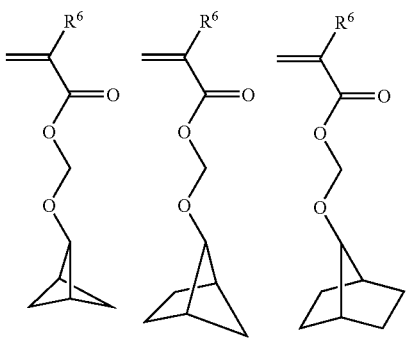

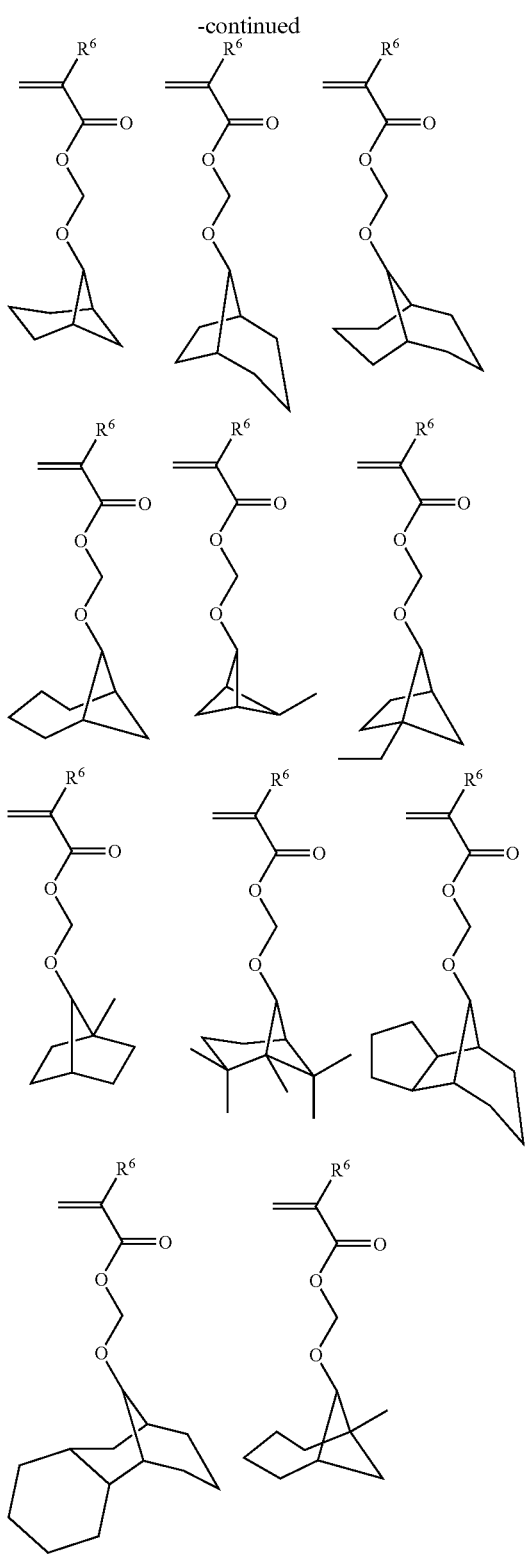

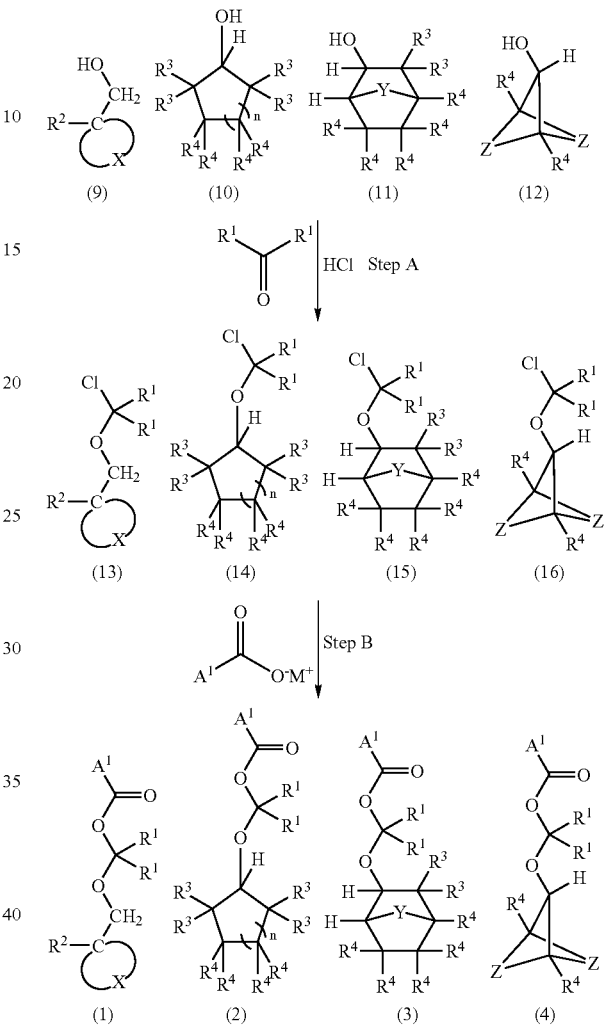

Herein $R^6$ is hydrogen, methyl or trifluoromethyl.

While the polymerizable acid-labile ester compounds of the invention have formulae (1) to (8) as defined above, they are prepared preferably by selecting an appropriate method in accordance with their structure. Specifically, they can be prepared, for example, by a two-stage synthesis method as shown below although the preparation method is not limited thereto. Now it is described how to prepare the polymerizable acid-labile ester compounds of the invention having formulae (1) to (4) as typical examples according to the scheme illustrated below.

Herein $A^1$ is a polymerizable functional group having a carbon-carbon double bond. $R^1$ is each independently hydrogen or $-C-(R^5)_3$. $R^2$ is a straight, branched or cyclic $C_1$-$C_{10}$ alkyl group. $R^3$ is each independently a straight, branched or cyclic $C_1$-$C_{10}$ alkyl group. $R^4$ is each independently hydrogen or a straight, branched or cyclic $C_1$-$C_{10}$ alkyl group. Alternatively, a combination of $R^3$, a combination of $R^4$, or a combination of $R^3$ and $R^4$ may bond together to form an aliphatic hydrocarbon ring with some carbon atoms in the ring to which they are attached, and in that event, each of $R^3$ and $R^4$ is a straight, branched or cyclic $C_1$-$C_{10}$ alkylene group. $R^5$ is each independently a straight, branched or cyclic monovalent hydrocarbon group of 1 to 10 carbon atoms. Alternatively, a combination of $R^5$ may bond together to form an aliphatic hydrocarbon ring with the carbon atom to which they are attached, and in that event, $R^5$ is a straight, branched or cyclic $C_2$-$C_{10}$ alkylene group. X is a straight, branched or cyclic $C_2$-$C_{20}$ alkylene group which forms an aliphatic hydrocarbon ring with the carbon atom to which it is attached at both ends. Y is a methylene, ethylene or isopropylidene group. Z is each independently a straight, branched or cyclic $C_1$-$C_{10}$ alkylene group which forms a 4- to 7-membered ring with the three-carbon chain to which it is attached at both ends, and n is 1 or 2. $R^1$ to $R^5$, X, Y, and Z are free of heteroatoms other than carbon and hydrogen atoms.

The first stage of reaction, designated "Step A" in the scheme, is a reaction of alcohol compounds (9) to (12) with a carbonyl compound: $R^1{}_2CO$ or an equivalent thereof and hydrogen chloride, to form 1-chloroalkyl ether compounds having formulae (13) to (16), respectively.

Examples of the carbonyl compound or equivalent thereof used in the reaction of Step A include aldehyde compounds such as formaldehyde, pivalaldehyde, and 1-adamantanecarbaldehyde, ketone compounds such as di-t-butyl ketone, and carbonyl compound equivalents such as paraformaldehyde and 1,3,5-trioxane. The amount of the carbonyl compound or equivalent thereof used is preferably 0.5 to 10 moles, and more preferably 1.0 to 2.0 moles per mole of the reactant, alcohol compound. With less than 0.5 mole of the carbonyl compound, a large proportion of the reactant may be left unreacted, leading to a substantial drop of yield. With more than 10 moles of the carbonyl compound, substantial side reactions may occur, reducing the yield and purity of the resulting 1-chloroalkyl ether compound.

A solvent may be used in the reaction of Step A. Suitable solvents include hydrocarbons such as toluene, xylene, hexane and heptane; and chlorinated solvents such as methylene chloride, chloroform and dichloroethane, which may be used alone or in admixture.

For the addition reaction described above, the reaction temperature may be selected as appropriate in accordance with other reaction conditions and is preferably in the range from $-70°$ C. to approximately the boiling point of the solvent, and more preferably in the range from $-20°$ C. to $20°$ C. The higher the reaction temperature, the more outstanding become side reactions. It is then important in attaining high yields that the reaction be carried out at as low a temperature as possible in the range for the reaction to proceed at a practically acceptable rate. Preferably the reaction time is determined so as to attain increased yields by monitoring the reaction process by gas chromatography (GC) or thin-layer chromatography (TLC). Usually, the reaction time is about 30 minutes to about 20 hours. The reaction is carried out by passing hydrogen chloride gas into a mixture of a reactant alcohol, a carbonyl compound or equivalent, and a solvent. After the completion of reaction and optionally the removal of the excess hydrogen chloride gas, an ordinary aqueous workup of the reaction mixture yields the intermediate product, 1-chloroalkyl ether compounds (13) to (16). If necessary, the intermediate compounds (13) to (16) may be purified by a standard technique such as recrystallization, chromatography or distillation, depending on the properties of a particular compound. Alternatively, simply after the water layer is removed by separatory operation, if necessary, the reaction mixture may be used in the subsequent step without further purification. This is preferred because the cost of manufacture is reduced by simplification of the process.

The second stage of reaction, designated "Step B" in the scheme, is an esterification reaction of the 1-chloroalkyl ether compounds (13) to (16) with carboxylic acid salts: $A^1CO_2^-\cdot M^+$. The reaction may be carried out by a standard esterification procedure using carboxylic acid salts and 1-chloroalkyl ether compounds. The carboxylic acid salt: $A^1CO_2^-\cdot M^+$ used herein may be selected from commercially available carboxylic acid salts, typically metal salts of carboxylic acids, or may be prepared in a reaction system using a carboxylic acid ($A^1CO_2H$) and a base. The amount of carboxylic acid salt: $A^1CO_2^-\cdot M^+$ used is preferably 0.5 to 10 moles, and more preferably 1.0 to 3.0 moles per mole of the reactant, alcohol compound. With less than 0.5 mole of the carboxylic acid salt, a large proportion of the reactant may be left unreacted, leading to a substantial drop of yield. Using more than 10 moles of the carboxylic acid salt may be uneconomical because of an increased cost of the salt and decreased pot yields. When the carboxylic acid salt is prepared in a reaction system using a carboxylic acid: $A^1CO_2H$ and a base, the base used herein may be selected from among amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium t-butoxide; organometallic compounds such as butyllithium and ethylmagnesium bromide; and metal amides such as lithium diisopropylamide, and mixtures thereof. The amount of the base used is preferably 0.2 to 10 moles, and more preferably 0.5 to 2.0 moles per mole of the carboxylic acid: $A^1CO_2H$. With less than 0.2 mole of the base, a large proportion of the carboxylic acid may run to waste, leading to a cost deficiency. With more than 10 moles of the base, substantial side reactions may occur, resulting in a substantial drop of yield.

A solvent may be used in the reaction of Step B. Suitable solvents include hydrocarbons such as toluene, xylene, hexane and heptane; chlorinated solvents such as methylene chloride, chloroform and dichloromethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, dimethyl sulfoxide; and water, which may be used alone or in admixture. To the reaction system, a phase transfer catalyst such as tetrabutylammonium hydrogen sulfate may be added. An appropriate amount of the phase transfer catalyst added is 0.0001 to 1.0 mole, and more preferably 0.001 to 0.5 mole per mole of the reactant, alcohol compound. Less than 0.0001 mole of the catalyst may exert little or no addition effect whereas more than 1.0 mole may be uneconomical because of an increased expense.

For the esterification reaction described above, the reaction temperature may be selected as appropriate in accordance with other reaction conditions and is preferably in the range from $-70°$ C. to approximately the boiling point of the solvent, and more preferably in the range from $0°$ C. to approximately the boiling point of the solvent. The higher the reaction temperature, the more outstanding become side reactions. It is then important in attaining high yields that the reaction be carried out at as low a temperature as possible in the range for the reaction to proceed at a practically acceptable rate. Preferably the reaction time is determined so as to attain increased yields by monitoring the reaction process by GC or TLC. Usually, the reaction time is about 30 minutes to about 40 hours. The reaction is carried out by mixing the 1-chloroalkyl ether compound (13) to (16) and the carboxylic acid salt in a solvent. After the completion of reaction, the target product, polymerizable acid-labile ester compounds (1) to (4) are obtainable through an ordinary aqueous workup or filtration of the salt formed and removal of the solvent. The target compounds (1) to (4) may be purified by a standard technique such as chromatography, distillation or recrystallization, depending on the properties of a particular compound.

Polymer

The polymers of the invention are characterized by comprising at least recurring units derived from one or more polymerizable acid-labile ester compounds having formulae (1) to (8) and having a weight average molecular weight (Mw) of 2,000 to 100,000, as measured by gel permeation chromatography (GPC) versus polystyrene standards. With Mw below 2,000, film formation, resolution and heat resistance may become poor. A polymer with Mw beyond 100,000 may become less soluble in a developer and poor in resolution, or generate many development defects. The Mw of the polymer may be controlled as appropriate by selecting polymerization and purifying formulations.

Specifically the polymers of the invention comprise recurring units having the formulae (1a) to (4a), and especially the formulae (5a) to (8a), shown below.

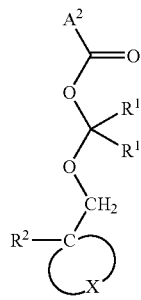
(1a)

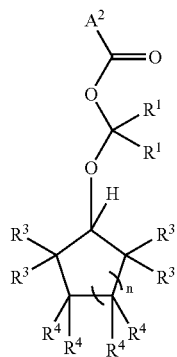
(2a)

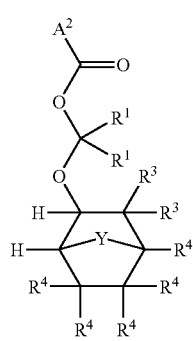
(3a)

-continued

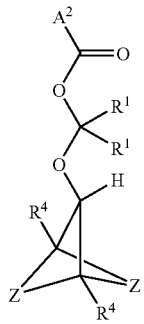
(4a)

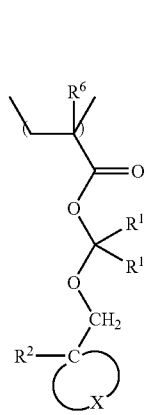
(5a)

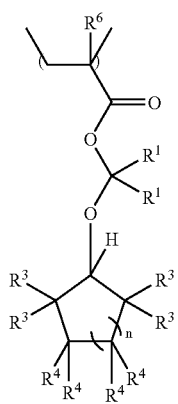
(6a)

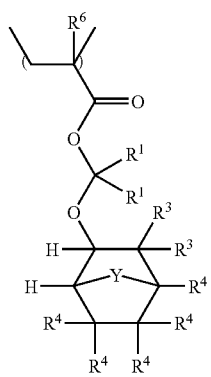
(7a)

-continued

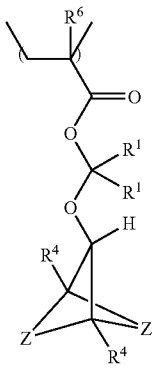

(8a)

Herein, $A^2$ is selected from the following groups.

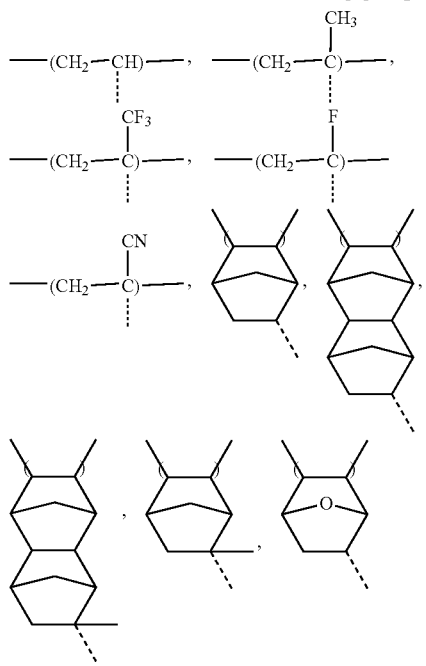

Note that $R^1$ to $R^4$, $R^6$, X, Y, Z, and n are as defined above, and the broken line indicates a bonding site.

If a polymer has an excess molecular weight distribution or dispersity (Mw/Mn), which indicates the presence of lower and higher molecular weight polymer components, there is a possibility that foreign matter is left on the pattern or the pattern profile is degraded. The influences of molecular weight and dispersity become stronger as the pattern rule becomes finer. Therefore, the multi-component copolymer should preferably have a dispersity (Mw/Mn) of 1.0 to 5.0, especially 1.0 to 2.5, in order to provide a resist composition suitable for micropatterning to a fine feature size.

The polymer can be synthesized by standard polymerization techniques including radical, anionic, cationic and coordination polymerization, and preferably radical polymerization. Specifically, a polymer may be obtained by adding any of polymerizable acid-labile ester compounds having formulae (1) to (8) and another comonomer to an organic solvent, adding a radical initiator thereto, and allowing radical polymerization to occur.

Examples of suitable organic solvents used herein include toluene, benzene, tetrahydrofuran, diethyl ether, dioxane, 2-butanone, ethyl acetate, 1-methoxy-2-propyl acetate, γ-butyrolactone, cyclohexanone, methyl isobutyl ketone and the like, which may be used alone or in admixture. Examples of suitable polymerization initiators used herein include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, and the like. Preferably the reaction mixture is heated to a temperature in the range from 40° C. to the boiling point of the solvent used. The reaction time is usually about 0.5 to 100 hours, and preferably about 1 to 30 hours.

If necessary, a thiol compound such as octane thiol, 2-mercaptoacetic acid, 3-mercaptopropionic acid or 2-mercaptoethanol, a disulfide compound such as dioctyl disulfide or the like may be added as a chain transfer agent during the reaction. The reaction may be carried out by mixing all components including monomers, an initiator, a solvent and an optional chain transfer agent and heating the mixture, or by heating a liquid comprising at least one component, feeding one or more other components individually or as a mixture to the heated liquid and heating the mixture. The latter method is preferred from the safety standpoint of preventing the reaction from running away. If necessary, the polymer may be taken out as solids by pouring the resulting polymerization solution to a poor solvent or otherwise causing the polymer to precipitate, and collecting the precipitate by filtration. Examples of the poor solvent used herein include alcohols such as methanol and 2-propanol, hydrocarbons such as hexane, heptane and toluene, water, and mixtures thereof.

In addition to the recurring units derived from the polymerizable acid-labile ester compounds having formulae (1) to (4) and especially formulae (5) to (8), the polymer may further comprise recurring units of at least one type selected from the following general formula (R1).

(R1)

Herein $R^{001}$ is hydrogen, fluorine, methyl, trifluoromethyl or $CH_2CO_2R^{003}$; $R^{002}$ is hydrogen, methyl or $CO_2R^{003}$; $R^{003}$ is a straight, branched or cyclic $C_1$-$C_{15}$ alkyl group; $R^{004}$ is hydrogen or a monovalent hydrocarbon group of 1 to 15 carbon atoms having at least one group selected from among fluorinated substituent groups, carboxyl, hydroxyl and cyano groups; at least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups, or a combination of $R^{005}$ to $R^{008}$ may bond together to form a ring, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to $R^{008}$ are each independently single bonds, hydrogen atoms or straight, branched or cyclic $C_1$-$C_{15}$ alkyl groups; $R^{009}$ is a monovalent hydrocarbon group of 3 to 15 carbon atoms containing a —$CO_2$— partial structure; at least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups, or a combination of $R^{010}$ to $R^{013}$ may bond together to form a ring, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups; $R^{014}$ is a polycyclic hydrocarbon group having 7 to 15 carbon atoms or an alkyl group containing such a polycyclic hydrocarbon group, $R^{015}$ is an acid labile group, and k is 0 or 1.

In formula (R1), $R^{001}$ is a hydrogen atom, fluorine atom, methyl group, trifluoromethyl group or $CH_2CO_2R^{003}$.

$R^{002}$ is a hydrogen atom, methyl group or $CO_2R^{003}$.

$R^{003}$ is a straight, branched or cyclic $C_1$-$C_{15}$ alkyl group, examples of which include methyl, ethyl, propyl, butyl, pentyl, hexyl, pentadecyl, isopropyl, sec-butyl, tert-butyl, tert-amyl, cyclic alkyls such as cyclopentyl, cyclohexyl, norbornyl, and adamantyl, and alkyl- or cycloalkyl-substituted derivatives thereof.

$R^{004}$ is a hydrogen atom or a monovalent hydrocarbon group of 1 to 15 carbon atoms having at least one group selected from among fluorinated substituent groups, carboxyl, hydroxyl and cyano groups. Examples include, but are not limited to, hydrogen, carboxymethyl, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, hydroxyadamantyl, dihydroxyadamantyl, [3,3,3-trifluoro-2-hydroxy-2-(trifluoromethyl)propyl]norbornyl, [2,2,2-trifluoro-1-hydroxy-1-(trifluoromethyl)ethyl]cyclohexyl, bis[2,2,2-trifluoro-1-hydroxy-1-(trifluoromethyl)ethyl]-cyclohexyl, cyanomethyl, cyanoethyl, cyanocyclohexyl, cyanonorbornyl, and cyanoadamantyl.

At least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups. Examples of suitable monovalent $C_1$-$C_{15}$ hydrocarbon groups having at least one group selected from among fluorinated substituent groups, carboxyl groups, hydroxyl groups and cyano groups include, but are not limited to, carboxymethyl, carboxyethyl, carboxybutyl, hydroxymethyl, hydroxyethyl, hydroxypropyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, hydroxyadamantyloxycarbonyl, dihydroxyadamantyloxycarbonyl, 3,3,3-trifluoro-2-hydroxy-2-(trifluoromethyl)propyl, 2,2,2-trifluoro-1-hydroxy-1-(trifluoromethyl)ethyl, [3,3,3-trifluoro-2-hydroxy-2-(trifluoromethyl)propyl]-norbornyloxycarbonyl, [2,2,2-trifluoro-1-hydroxy-1-(trifluoromethyl)ethyl]-cyclohexyloxycarbonyl, bis[2,2,2-trifluoro-1-hydroxy-1-(trifluoromethyl)ethyl]-cyclohexyloxycarbonyl, cyano, cyanomethyl, cyanoethyl, and cyanomethyloxycarbonyl. Suitable straight, branched or cyclic $C_1$-$C_{15}$, alkyl groups represented by $R^{005}$ to $R^{008}$ are as exemplified for $R^{003}$.

Any two or more of $R^{005}$ to $R^{008}$ may bond together to form a ring, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to $R^{008}$ are each independently single bonds, hydrogen atoms or straight, branched or cyclic $C_1$-$C_{15}$ alkyl groups. Suitable divalent $C_1$-$C_{15}$ hydrocarbon groups having at least one group selected from fluorinated substituent groups, carboxyl, hydroxyl and cyano groups include those exemplified above as the monovalent hydrocarbon groups having at least one group selected from fluorinated substituent groups, carboxyl, hydroxyl and cyano groups, with one hydrogen atom eliminated therefrom.

$R^{009}$ is a monovalent hydrocarbon group of 3 to 15 carbon atoms containing a —$CO_2$— partial structure. Examples include, but are not limited to, 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups. Illustrative examples of suitable monovalent $C_2$-$C_{15}$ hydrocarbon groups containing a —$CO_2$— partial structure include, but are not limited to, methoxycarbonyl, ethoxycarbonyl, 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Suitable straight, branched or cyclic $C_1$-$C_{15}$ alkyl groups are as exemplified for $R^{003}$.

Any two or more of $R^{010}$ to $R^{013}$ may bond together to form a ring, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups. Illustrative examples of suitable divalent $C_1$-$C_{15}$ hydrocarbon groups containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as those exemplified as the monovalent hydrocarbon groups containing a —$CO_2$— partial structure, with one hydrogen atom eliminated therefrom.

$R^{014}$ is a polycyclic hydrocarbon group having 7 to 15 carbon atoms or an alkyl group containing such a polycyclic hydrocarbon group. Examples include norbornyl, bicyclo[3.3.1]nonyl, tricyclo[5.2.1.0$^{2,6}$]decyl, adamantyl, decahydronaphthalenyl, tetracyclo[6.2.1.1$^{3,6}$.0$^{2,7}$]dodecyl, cyclohexylmethyl, adamantylmethyl, and alkyl- or cycloalkyl-substituted derivatives thereof.

R$^{015}$ is an acid labile group. The acid labile group may be selected from a variety of such groups. It is a group to be deprotected by the acid generated from the photoacid generator to be described later and may be any of well-known acid labile groups which are commonly used in prior art resist compositions, especially chemically amplified resist compositions. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

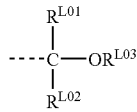

(L1)

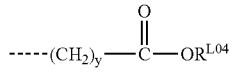

(L2)

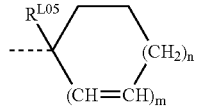

(L3)

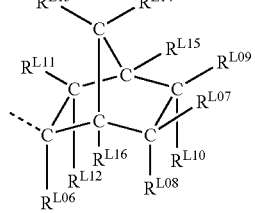

(L4)

Herein the broken line denotes a valence bond. R$^{L01}$ and R$^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, adamantyl, and adamantylmethyl. R$^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples of the straight, branched or cyclic alkyl groups are as exemplified above for R$^{L01}$ and R$^{L02}$, and examples of the substituted alkyl groups are as shown below.

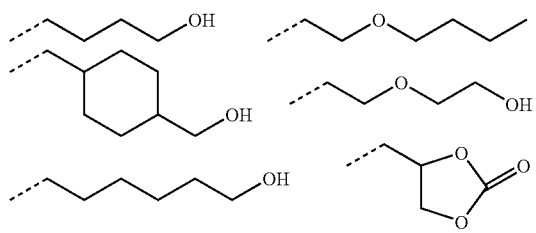

A pair of R$^{L01}$ and R$^{L02}$, R$^{L01}$ and R$^{L03}$, or R$^{L02}$ and R$^{L03}$ may bond together to form a ring with carbon and oxygen atoms to which they are attached. Each of R$^{L01}$, R$^{L02}$ and R$^{L03}$ is a straight or branched alkylene group of 1 to 18 carbon atoms, preferably 1 to 10 carbon atoms when they form a ring.

R$^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 2-(tricyclo[5.2.1.0$^{2,6}$]decan-8-yl)propan-2-yl, 2-(tetracyclo[4.4.0.1$^{2,5}$.1$^{7,10}$]dodecan-3-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,}$ $_{5}$.1$^{7,10}$]dodecyl, 3-ethyl-3-tetracyclo[4.4.0.1$^{2,5}$.1$^{7,10}$]dodecyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), R$^{L05}$ is an optionally substituted, straight, branched or cyclic C$_1$-C$_{10}$ alkyl group or an optionally substituted C$_6$-C$_{20}$ aryl group. Examples of the optionally substituted alkyl groups include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxy, alkoxycarbonyl, oxo, amino, alkylamino, cyano, mercapto, alkylthio, sulfo or other groups or in which some methylene groups are replaced by oxygen or sulfur atoms. Examples of optionally substituted aryl groups include phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), R$^{L06}$ is an optionally substituted, straight, branched or cyclic C$_1$-C$_{10}$ alkyl group or an optionally substituted C$_6$-C$_{20}$ aryl group. Examples of these groups are the same as exemplified for R$^{L05}$. R$^{L07}$ to R$^{L16}$ independently represent hydrogen or monovalent hydrocarbon groups of 1 to 15 carbon atoms. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, R$^{L07}$ to R$^{L16}$ may bond together to form a ring (for example, a pair of R$^{L07}$ and R$^{L08}$, R$^{L07}$ and R$^{L09}$, R$^{L08}$ and R$^{L10}$, R$^{L09}$ and R$^{L10}$, R$^{L11}$ and R$^{L12}$, R$^{L13}$ and R$^{L14}$, or a similar pair form a ring). Each of R$^{L07}$ to R$^{L16}$ represents a divalent C$_1$-C$_{15}$ hydrocarbon group when they form a ring, examples of which are those exemplified above for the monovalent hydrocarbon groups, with one hydrogen atom being eliminated. Two of R$^{L07}$ to R$^{L16}$ which are attached to vicinal carbon atoms may bond together directly to form a double bond (for example, a pair of R$^{L07}$ and R$^{L09}$, R$^{L09}$ and R$^{L15}$, R$^{L13}$ and R$^{L15}$, or a similar pair).

Of the acid labile groups of formula (L1), the straight and branched ones are exemplified by the following groups.

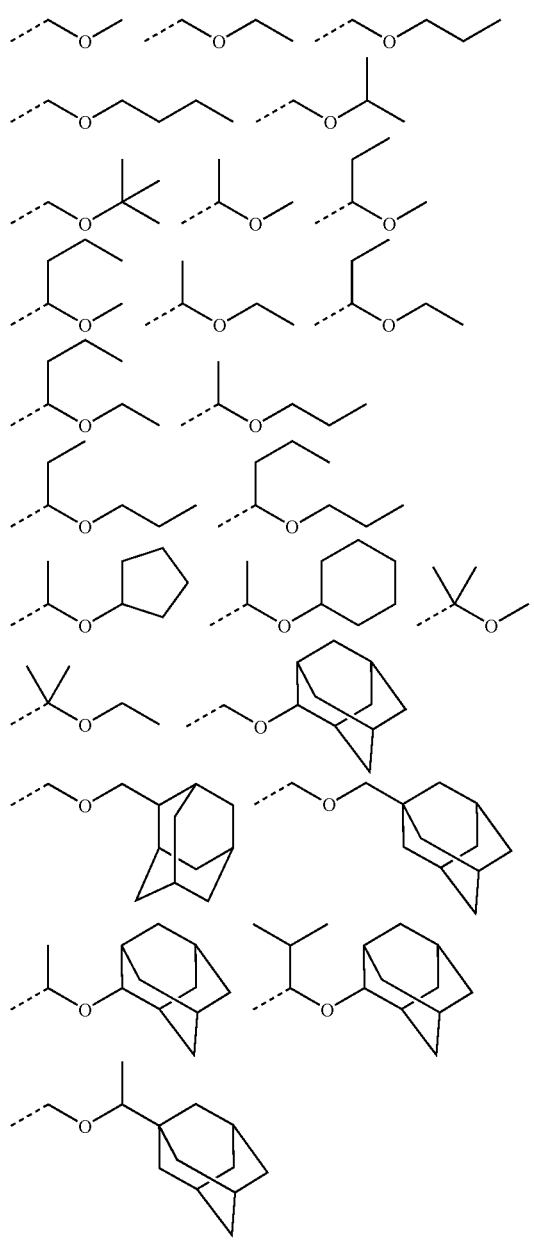

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxybutyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 1-methyl-2-cyclopentenyl, 1-ethyl-2-cyclopentenyl, 1-methyl-2-cyclohexenyl, and 1-ethyl-2-cyclohexenyl groups.

Of the acid labile groups of formula (L4), those groups of the following formulae (L4-1) to (L4-4) are preferred.

(L4-1)

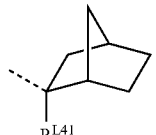

(L4-2)

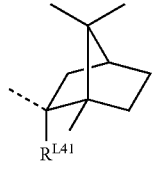

(L4-3)

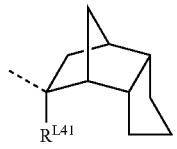

(L4-4)

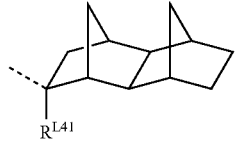

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

(L4-3-1)

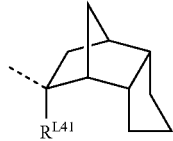

(L4-3-2)

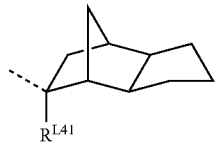

Similarly, the general formula (L4-4) represents one or a mixture of two or more selected from groups having the following general formulas (L4-4-1) to (L4-4-4).

(L4-4-1)

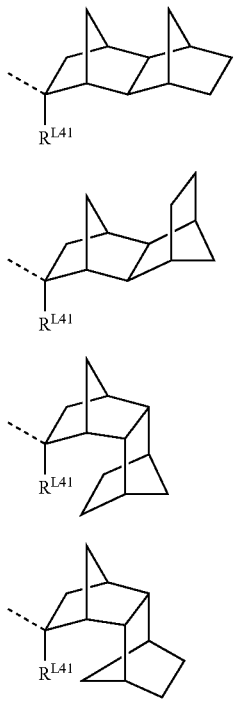

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

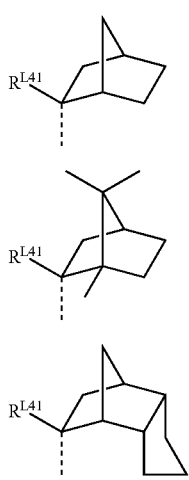

(L4-2-endo)

(L4-3-endo)

-continued (L4-4-endo)

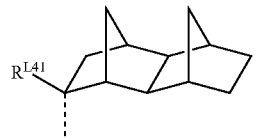

Illustrative examples of the acid labile group of formula (L4) are given below.

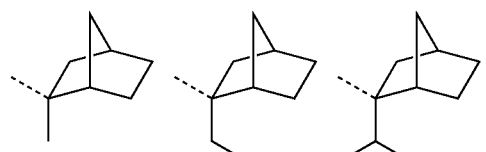

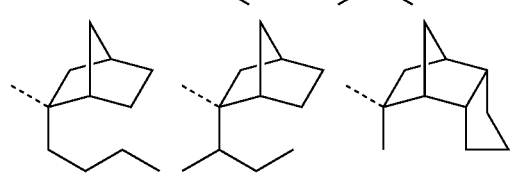

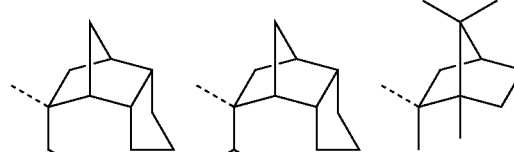

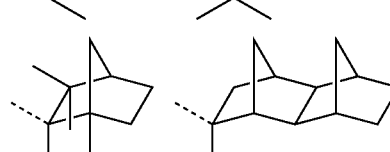

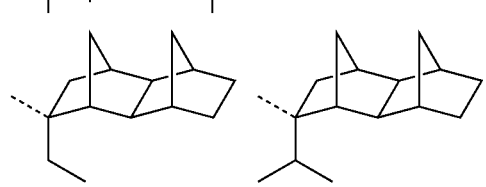

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{LO4}$ and the like.

In formula (R1), letters a1', a2', b1', b2', c1', c2', d1', d2', and e' are numbers from 0 to less than 1 and indicate proportions of corresponding recurring units relative to the total recurring units of a polymer.

With respect to the recurring units in formula (R1), units of more than one type may be incorporated at the same time. Incorporation of units of more than one type enables to adjust the performance of a resist material in which the resulting polymer is formulated.

Such resist properties as acid diffusion length, developer affinity and contact angle may be adjusted by incorporating into a polymer recurring units of at least one type selected from the recurring units incorporated at compositional ratio a1' in formula (R1). Examples of these units are given below, but not limited thereto.

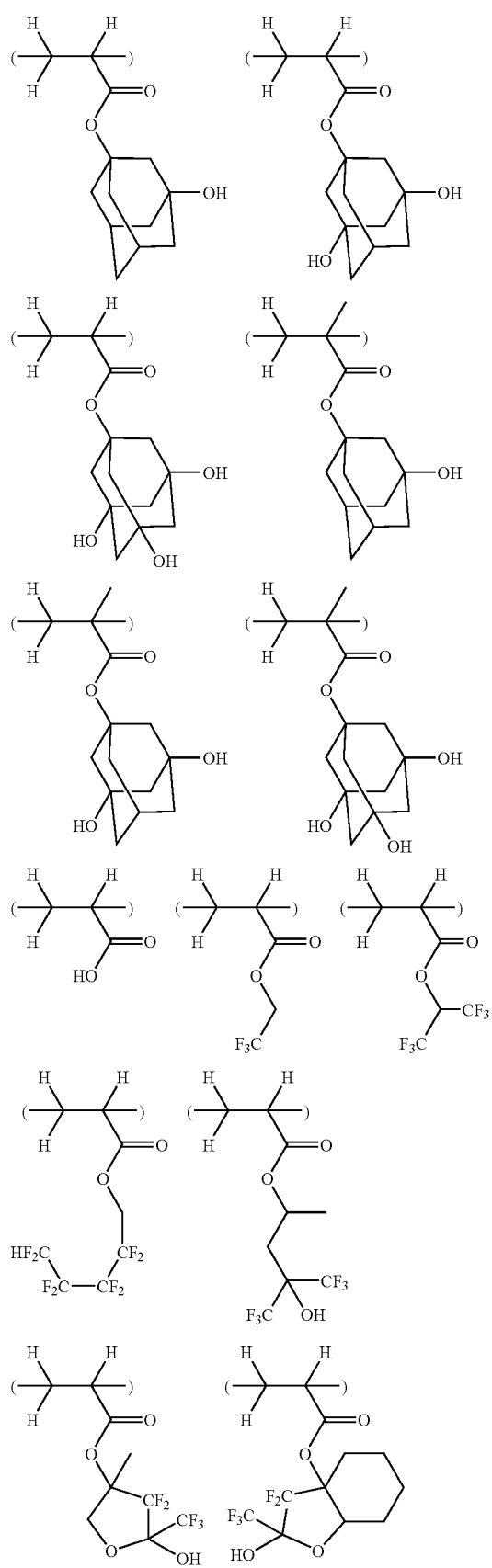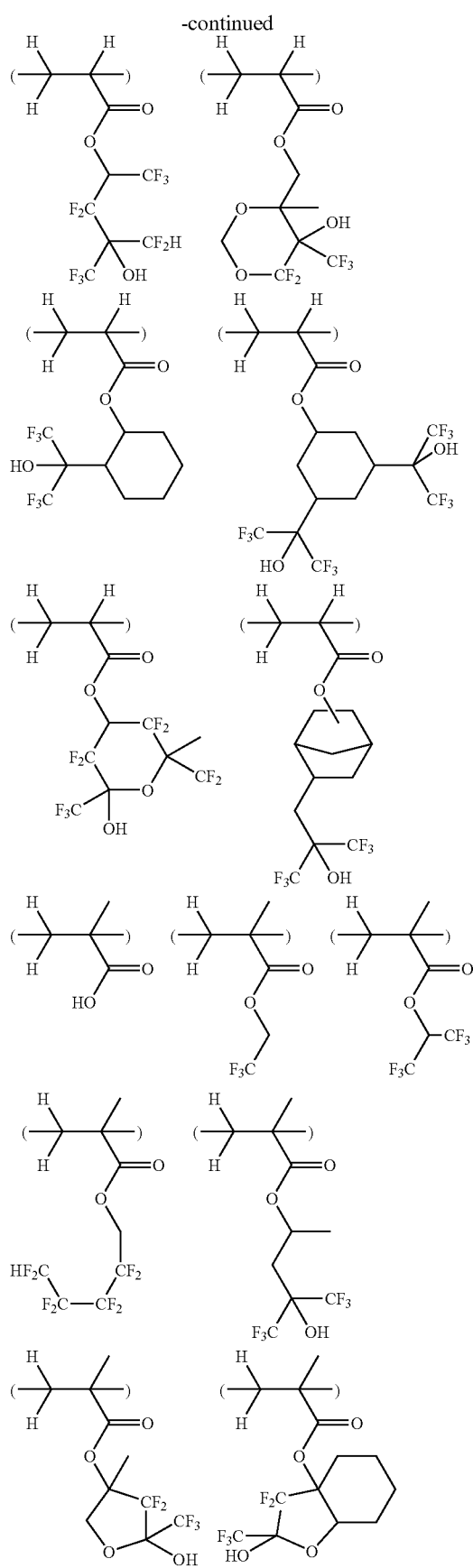

-continued
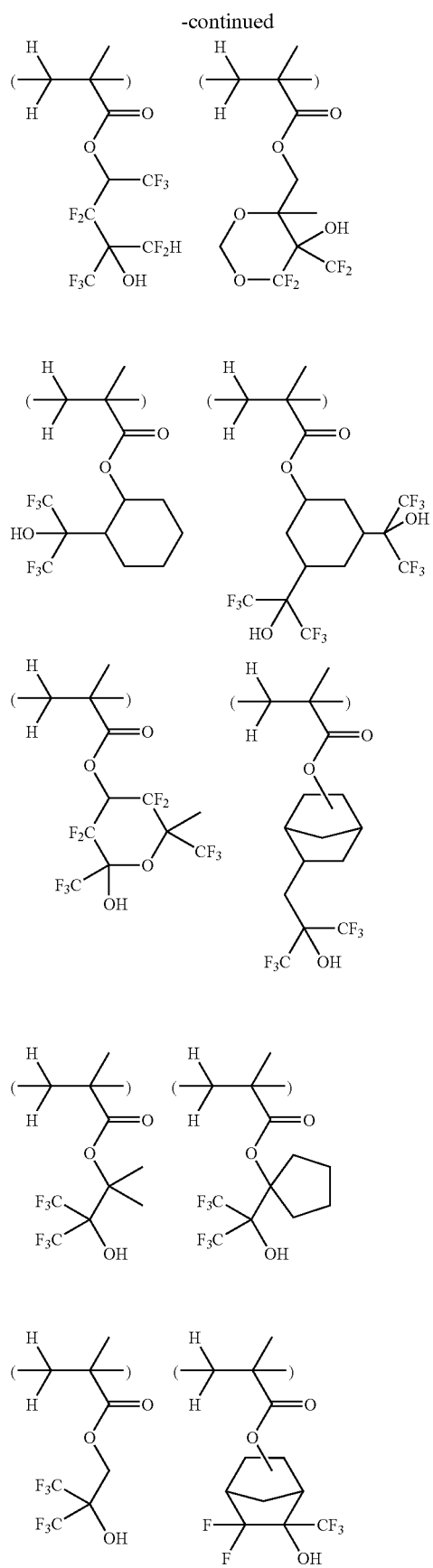
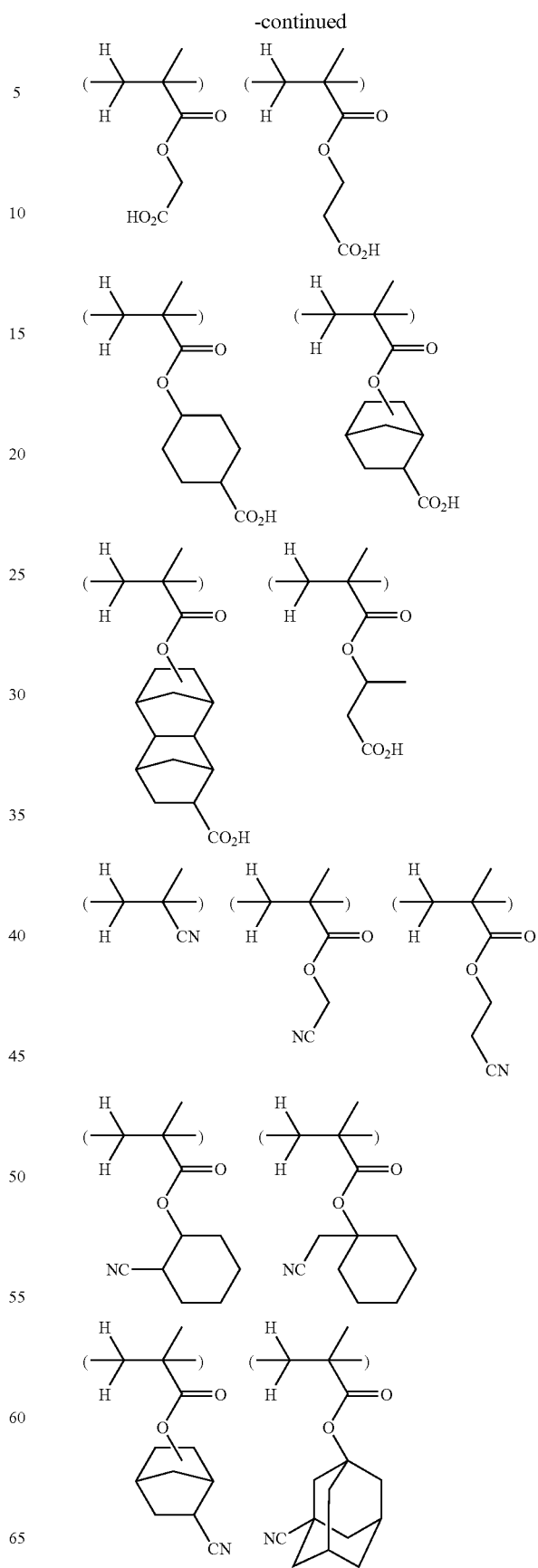

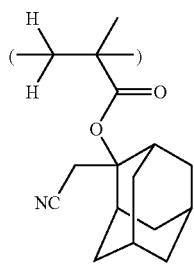
The substrate adhesion of resist patterns may be improved by incorporating into a polymer recurring units of at least one type selected from the recurring units incorporated at compositional ratio b1' in formula (R1). Examples of these units are given below, but not limited thereto.
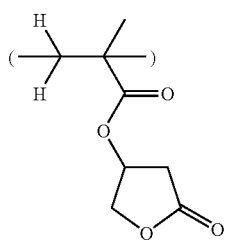 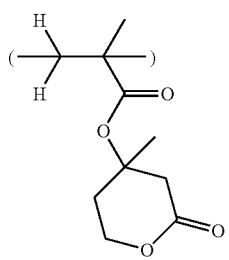
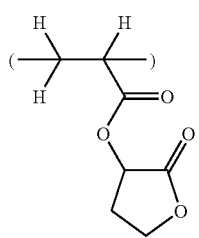 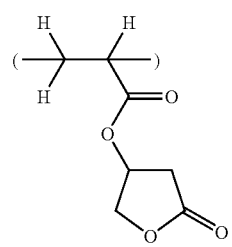
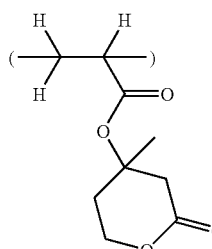 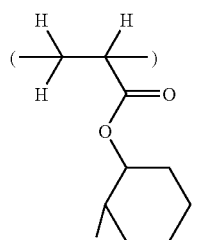
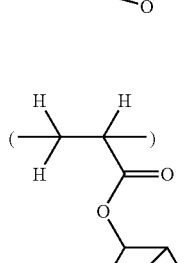 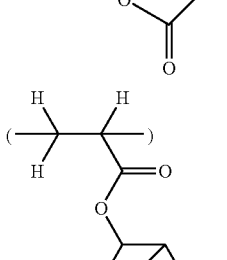
 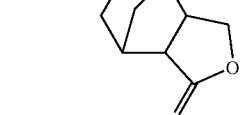

-continued
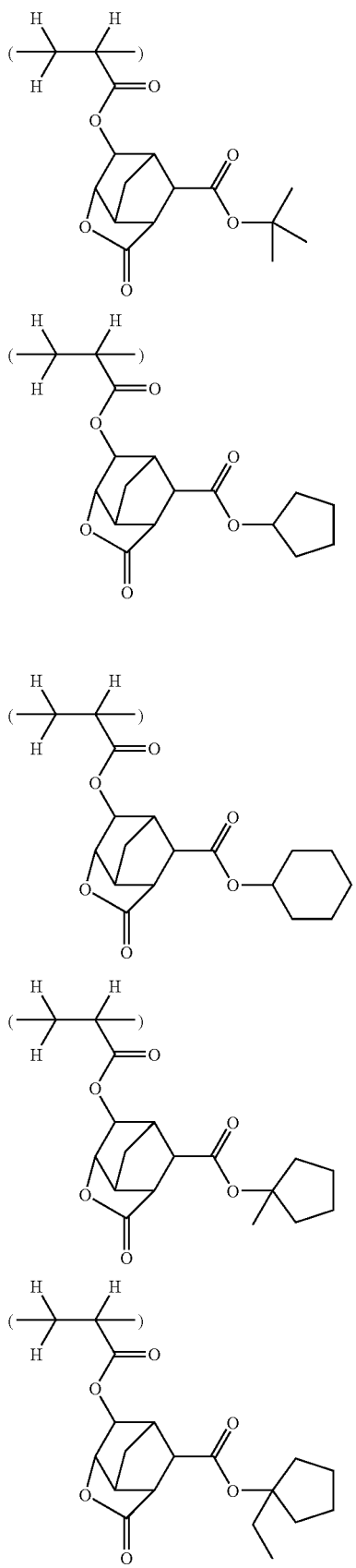
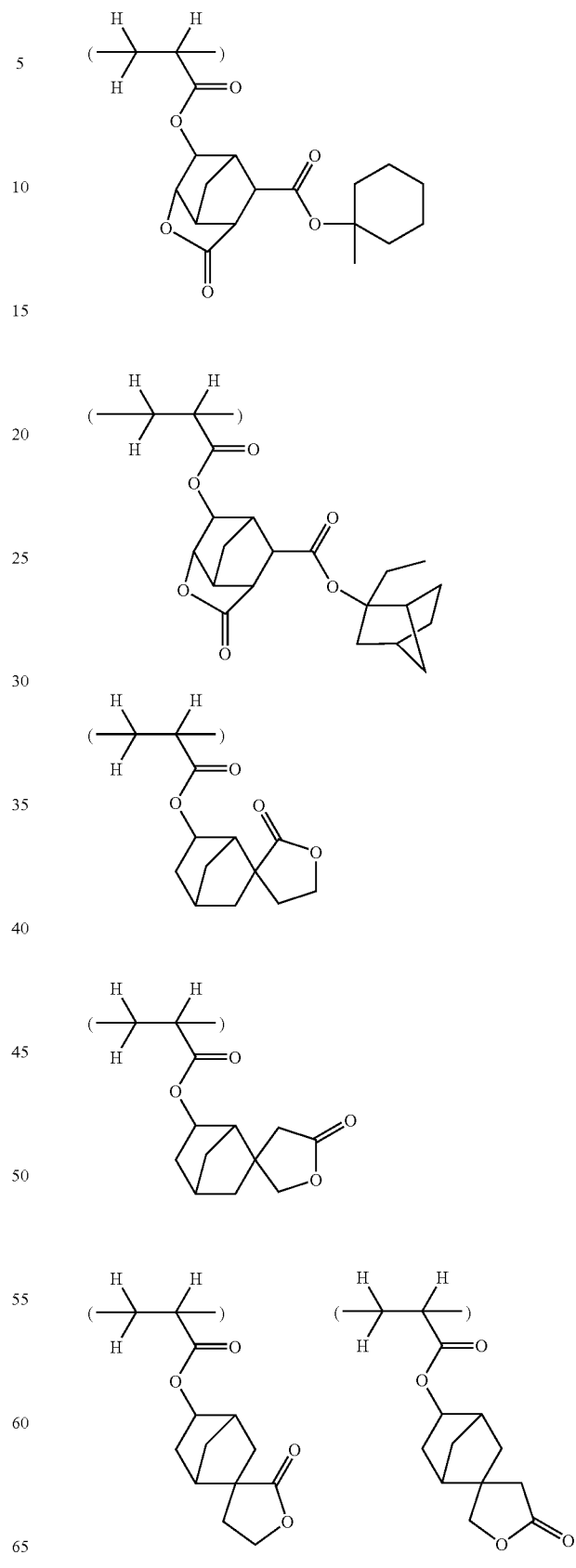

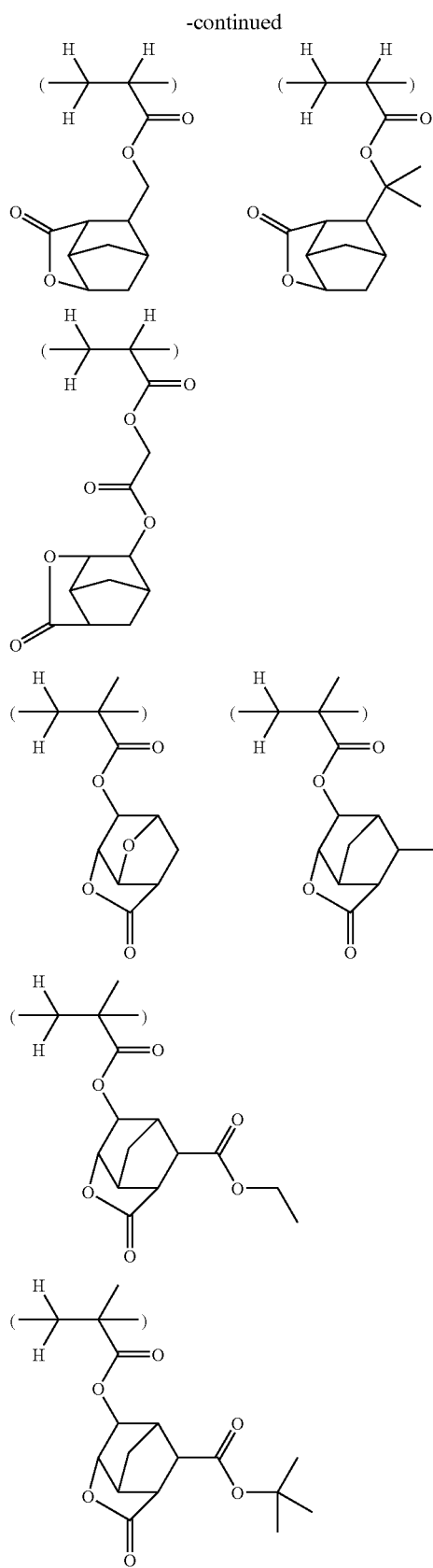
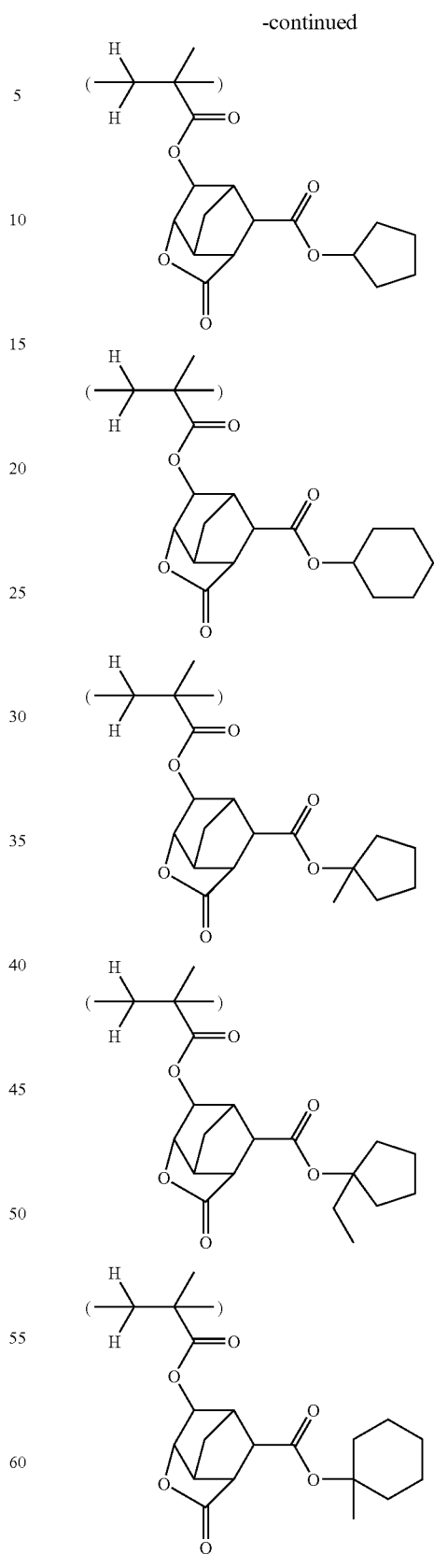

-continued
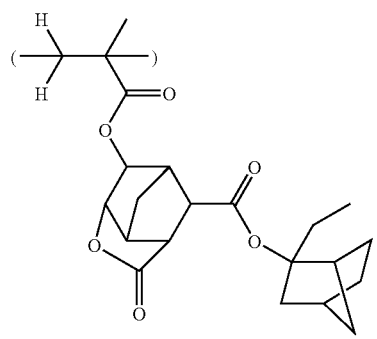
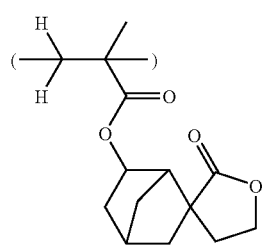
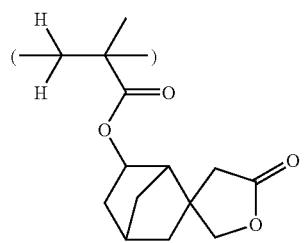
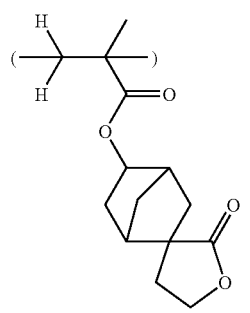
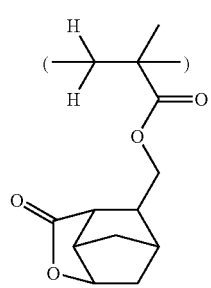
-continued
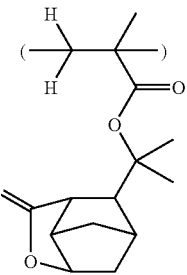
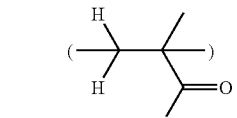
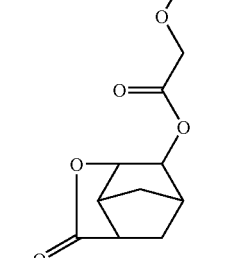
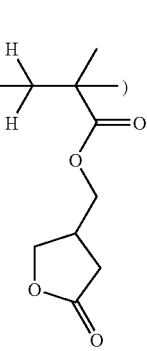
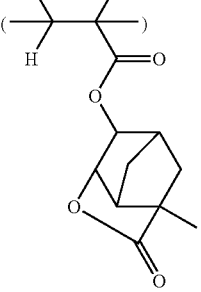
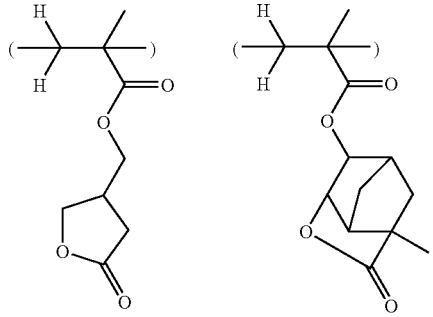
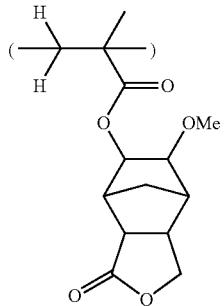
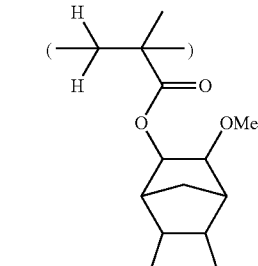
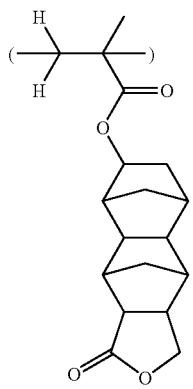
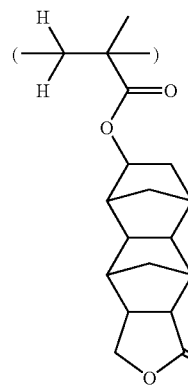
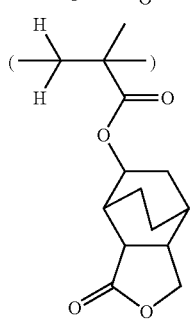
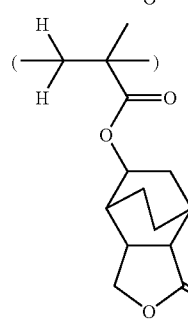

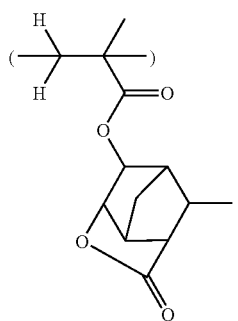
Such resist properties as dissolution contrast may be adjusted by incorporating into a polymer recurring units of at least one type selected from the recurring units incorporated at compositional ratio d1' in formula (R1). Examples of these units are given below, but not limited thereto.
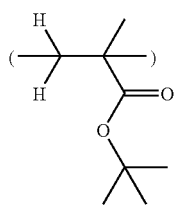 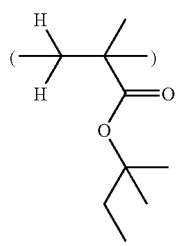
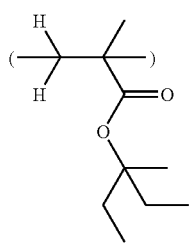 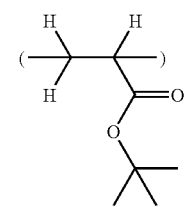
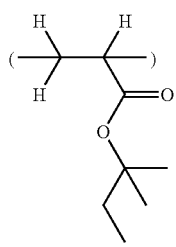 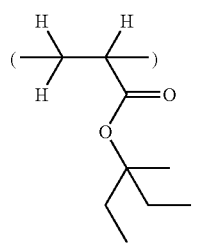
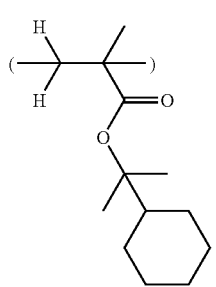 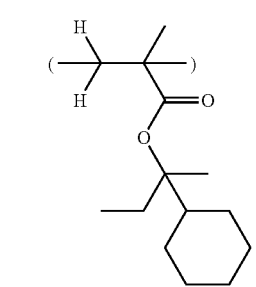
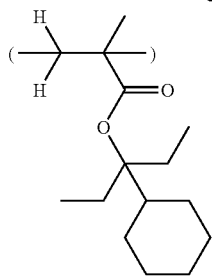 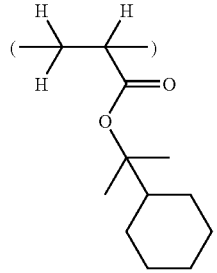
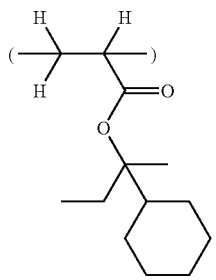 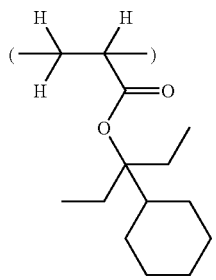
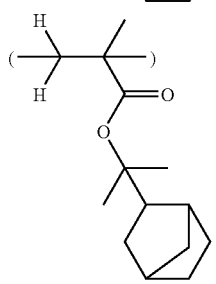 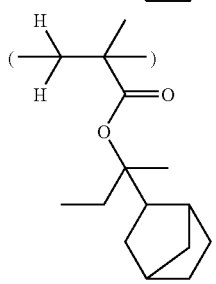
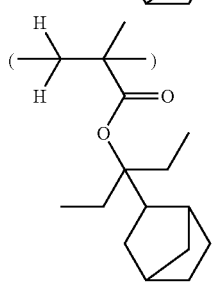 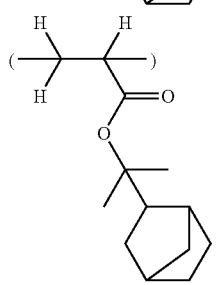
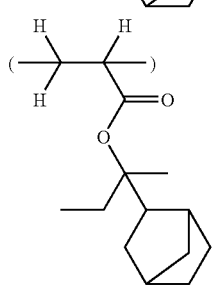 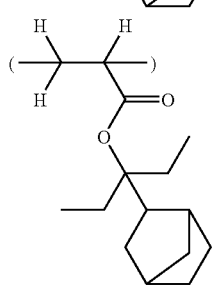
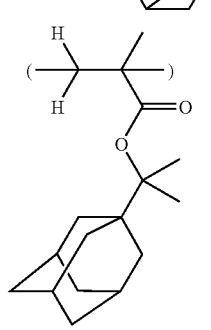 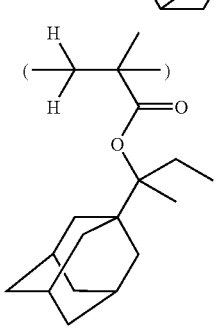

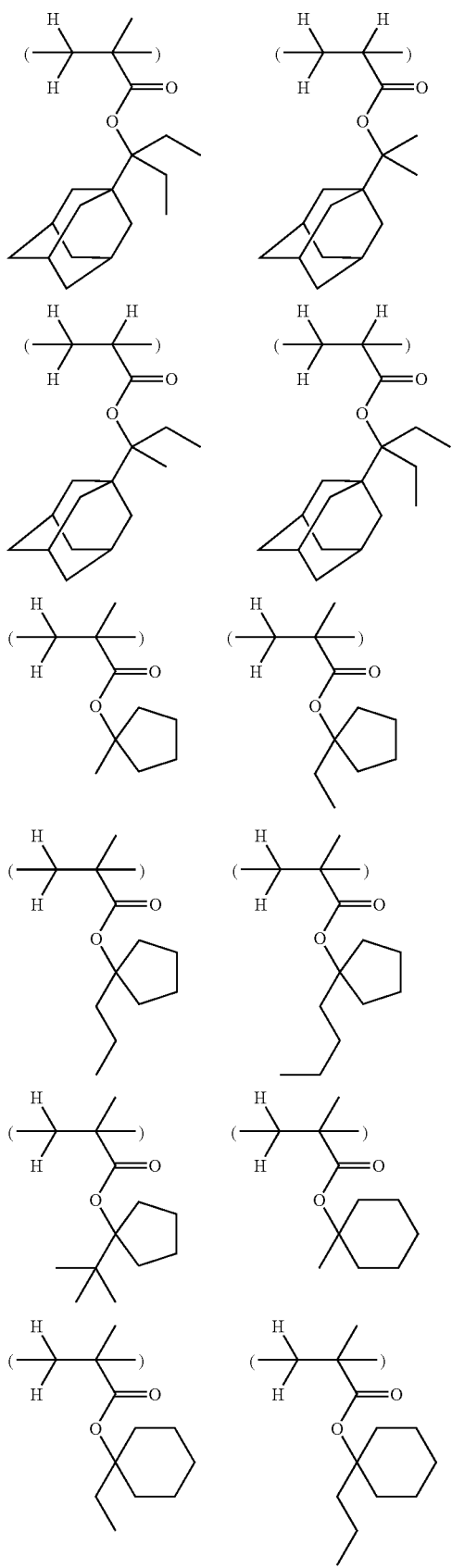
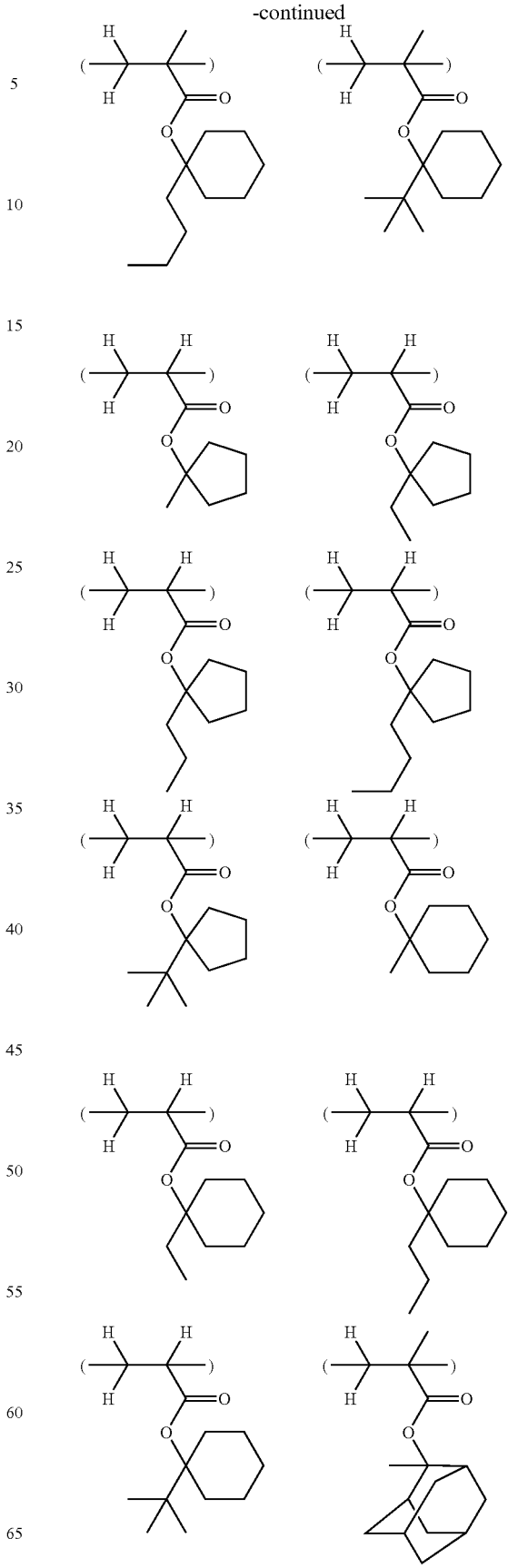

-continued
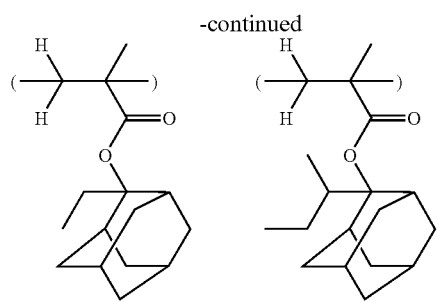
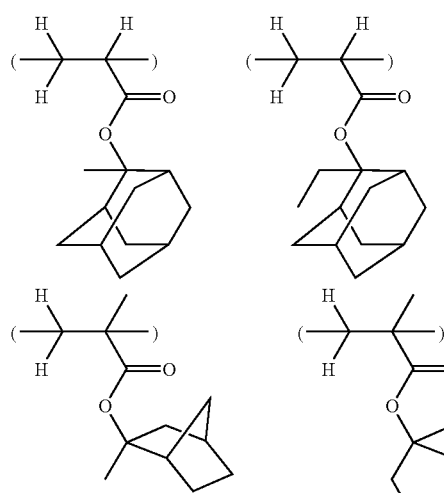
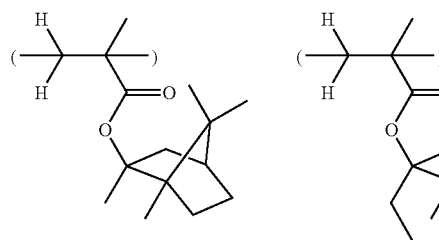
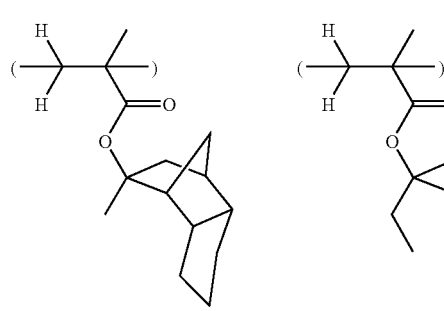
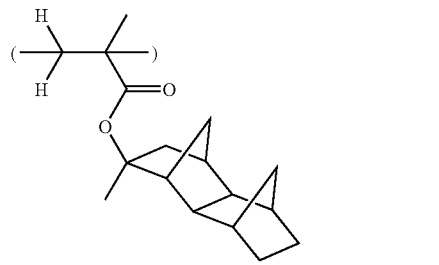
-continued
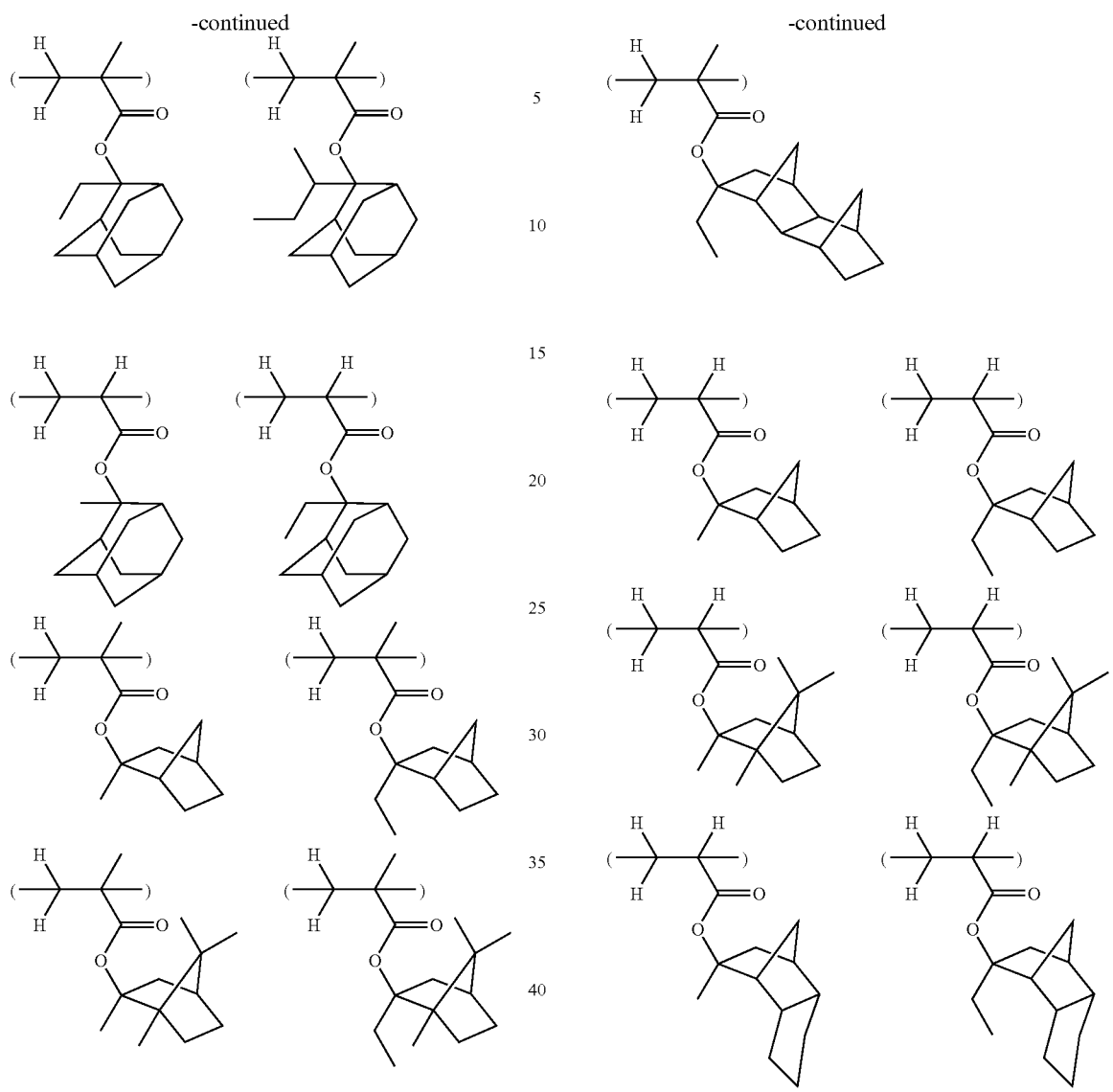
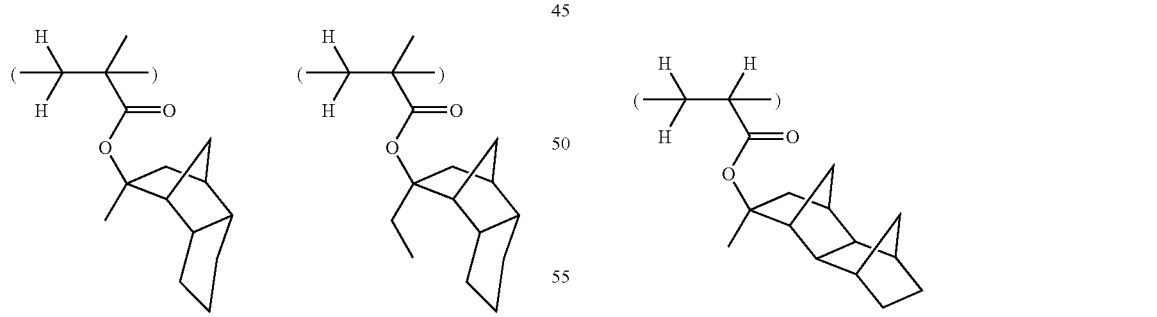
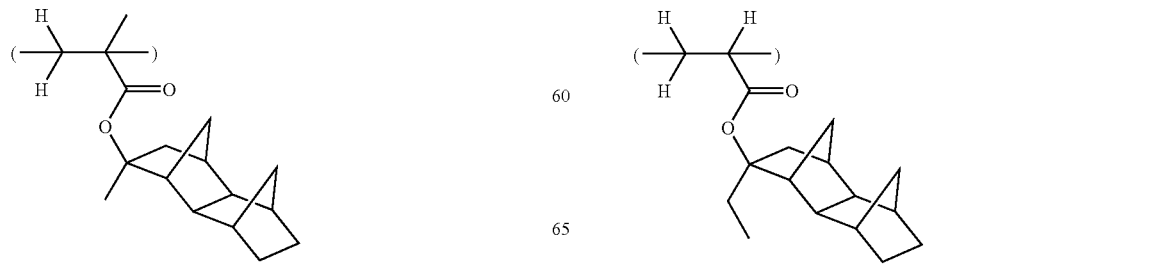

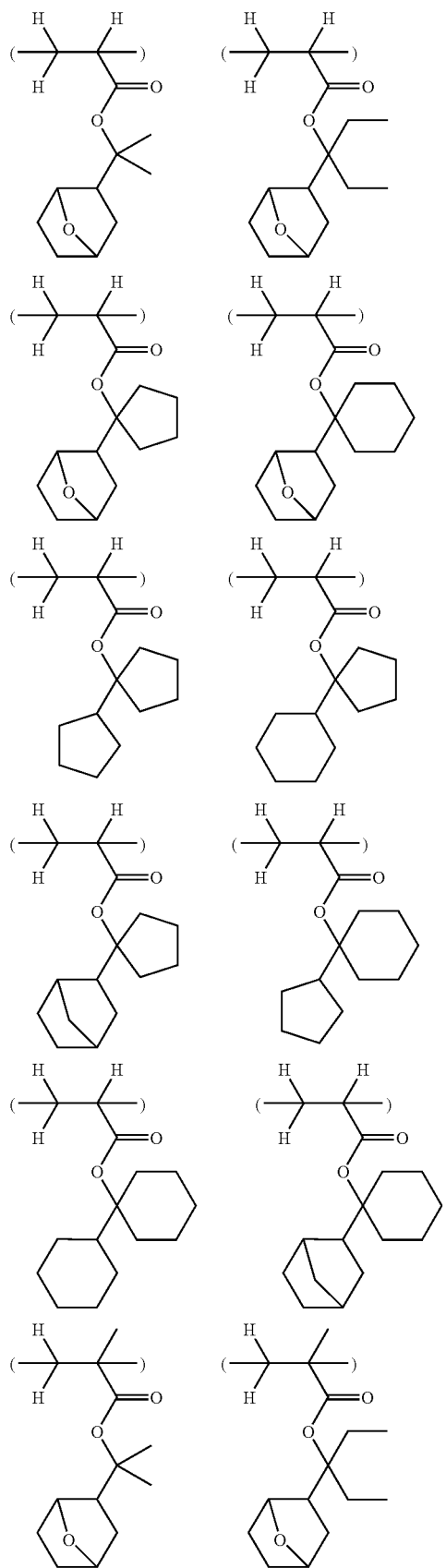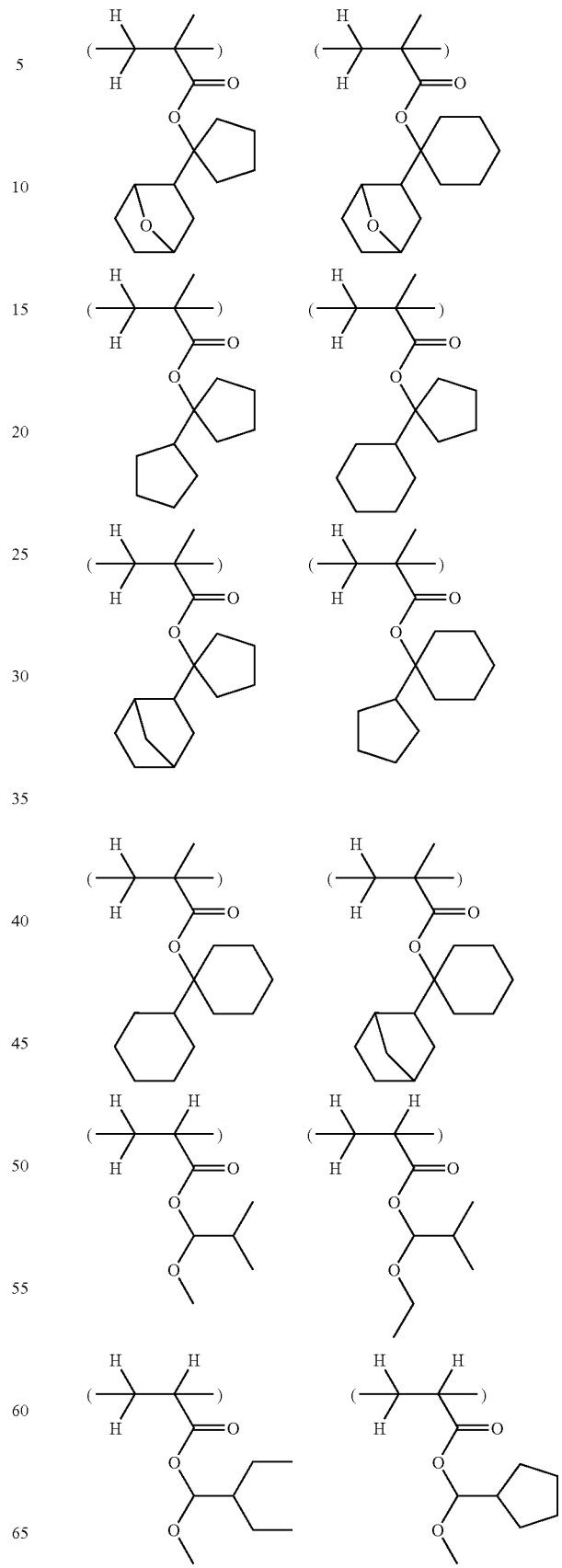

-continued
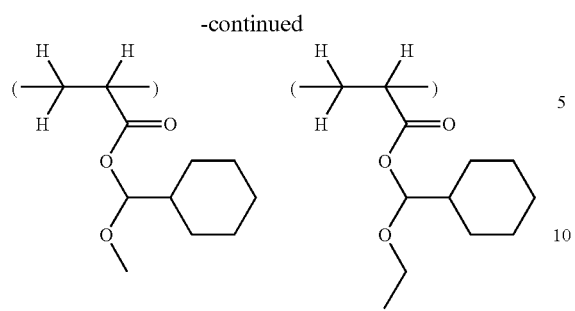
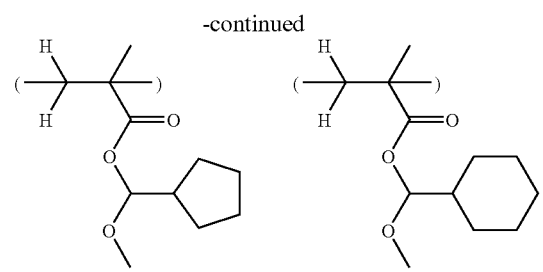
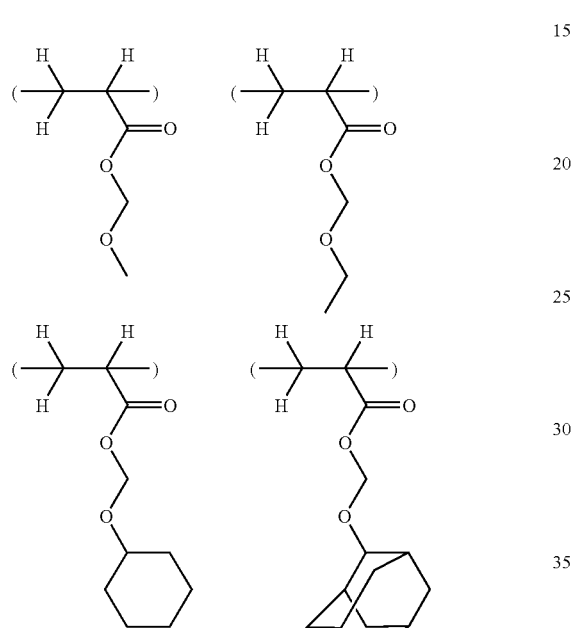
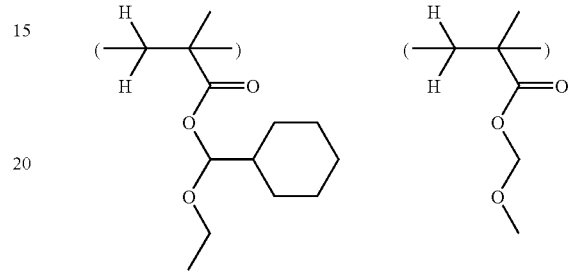
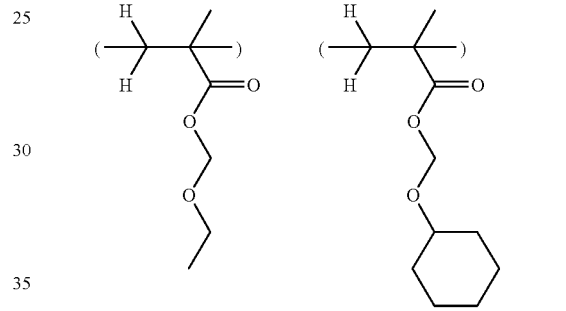
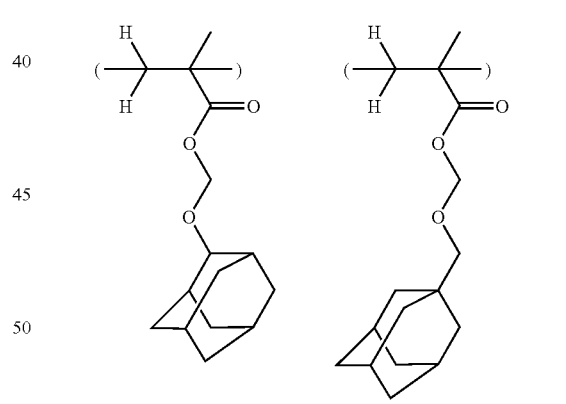
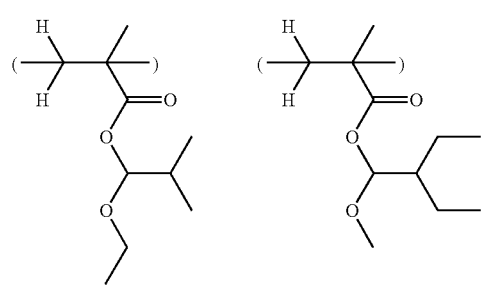
The polymer of the invention may further comprise recurring units of at least one type selected from the following general formula (R2).
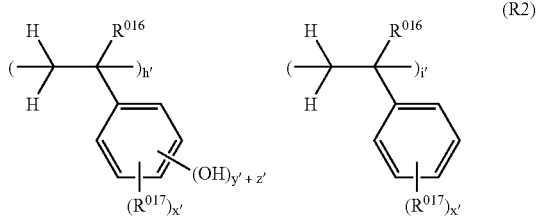
(R2)

-continued

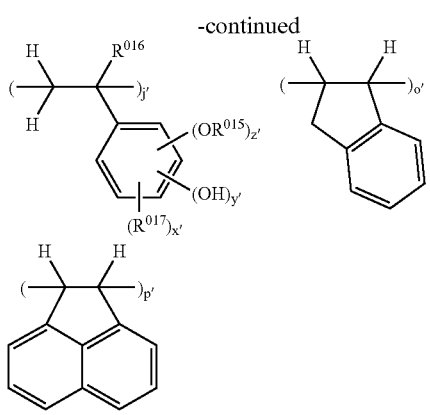

Herein, $R^{015}$ is as defined above, $R^{016}$ is hydrogen or methyl. $R^{017}$ is a straight, branched or cyclic $C_1$-$C_8$ alkyl group, f', g', h', i', j', o', and p' indicative of ratios of corresponding recurring units to the total recurring units in the polymer are numbers from 0 to less than 1, x', y', and z' each are an integer of 0 to 3, satisfying $1 \leq x'+y'+z' \leq 5$ and $1 \leq y'+z' \leq 3$.

Preferably the polymer of the invention comprises recurring units of formulae (1a) to (8a) in a molar fraction of 5% to 70%. Incorporation of the recurring units in a molar fraction of less than 5% fails to exert their effect whereas a fraction of more than 70% may lead to an extra extension of acid diffusion length and a degraded resolution. In the polymer, recurring units of one or more types selected from formulae (1a) to (8a) may be present.

In the polymers of the invention, the preferred proportion of recurring units derived from the respective monomers is in the following range (in mol %), though not limited thereto. The polymers contain:

(I) from 5 mol % to 70 mol %, more preferably 10 mol % to 50 mol % of constituent units having one or more of formulae (1a) to (4a) derived from the monomers of formulae (1) to (4), especially constituent units having one or more of formulae (5a) to (8a) derived from the monomers of formulae (5) to (8),
(II) from 0 mol % to 95 mol %, more preferably 5 mol % to 90 mol %, and even more preferably 10 mol % to 80 mol % of constituent units of one or more types in formula (R1), and
(III) from 0 mol % to 95 mol %, more preferably 0 mol % to 90 mol %, and even more preferably 0 mol % to 80 mol % of constituent units of one or more types derived from another monomer(s), i.e., in formula (R2).

It is noted that of the recurring units in formula (R1), those recurring units incorporated at compositional ratios a1' and b1' in formula (R1) are preferred.

The polymer of the invention can be formulated as a base resin into a chemically amplified positive working resist composition. It is understood that on use of the polymer as the base resin, a blend of two or more polymers which differ in recurring unit type, compositional ratio, molecular weight or molecular weight distribution is acceptable. The inventive polymer may also be used as a blend with any of conventional polymers including (meth)acrylate copolymers, (meth)acrylate/vinyl ether/maleic anhydride copolymers (VEMA), cycloolefin/maleic anhydride copolymers (COMA), polynorbornene, and hydrogenated cycloolefin ring-opening metathesis polymers (hydrogenated ROMP). In particular, COMA, polynorbornene, and hydrogenated ROMP, derived from cycloolefin monomers are characterized by high etching resistance and a minimal change of pattern feature size with varying PEB temperature (i.e., minimized PEB temperature dependence), and blends thereof with the inventive (meth)acrylate polymers featuring a high resolution lead to resist compositions having both a high resolution and high etching resistance. Illustrative, non-limiting examples of the polymers derived from cycloolefin monomers are given below.

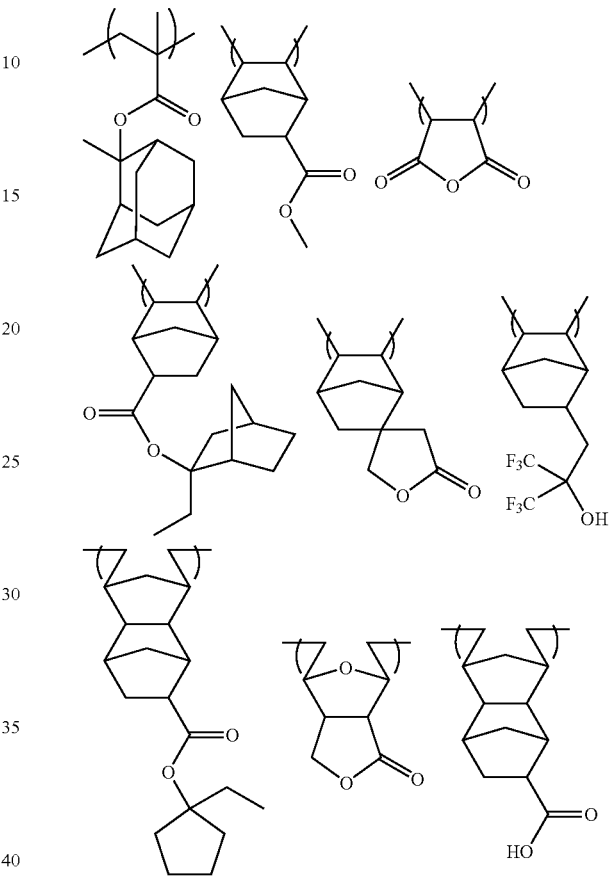

Resist Composition

The polymer of the invention is useful as a base resin in chemically amplified positive resist compositions. Then the other aspect of the invention provides a chemically amplified positive resist composition comprising the polymer. Typically, the resist composition comprises (A) the polymer, (B) a photoacid generator, (C) an organic solvent, and optionally (D) a sensitivity regulator and (E) a surfactant.

While the polymer of the invention is useful as the base resin (A), any of well-known resins having a rate of dissolution in an alkaline developer that increases under the action of an acid may be added if desired. In a preferred embodiment, the polymer of the invention accounts for 10 to 100% by weight, more preferably 30 to 100% by weight, and even more preferably 40 to 100% by weight based on the total base resin.

Photoacid Generator

The photoacid generator (PAG) may be any compound which generates an acid upon exposure to high-energy radiation and specifically, any of well-known photoacid generators which are commonly used in prior art resist compositions, especially chemically amplified resist compositions. Suitable photoacid generators include sulfonium salts, iodonium salts, sulfonyldiazomethane, N-sulfonyloxyimide, and oxime-O- sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butbxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Exemplary bis(substituted alkylsulfonyl)imides include bis-trifluoromethylsulfonylimide, bispentafluoroethylsulfonylimide, bisheptafluoropropylsulfonylimide, and perfluoro-1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2.5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Exemplary bis(substituted alkylsulfonyl)imides include bis-trifluoromethylsulfonylimide, bispentafluoroethylsulfonylimide, bisheptafluoropropylsulfonylimide, and perfluoro-1,3-propylenebissulfonylimide.

A typical tris(substituted alkylsulfonyl)methide is tristrifluoromethylsulfonylmethide. Iodonium salts based on combination of the foregoing examples are included.

Exemplary sulfonyldiazomethane compounds include bissulfonyldiazomethane compounds and sulfonylcarbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis (2-methyl-5-isopropyl-4-(n-hexyloxy)phenylsulfonyl)-diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo[2.2.1]-5-heptene-2,3-dicarboxylic acid imide. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucinol, catechol, resorcinol, and hydroquinone, in which all the hydroxyl groups are substituted by trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are the oxime sulfonates described in U.S. Pat. No. 6,004,724, for example, (5-(4-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc. Also included are the oxime sulfonates described in U.S. Pat. No. 6,916,591, for example, (5-(4-(4-toluenesulfonyloxy)benzenesulfonyl)oxyimino-5H-thiophen-2-ylidene)phenylacetonitrile and (5-(2,5-bis(4-toluenesulfonyloxy)benzenesulfonyl)oxyimino-5H-thiophen-2-ylidene)phenylacetonitrile. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropane-sulfonate, 2-acetyloxy-1,1,3,3,3-pentafluoropropane-sulfonate, 1,1,3,3,3-pentafluoro-2-hydroxypropane-sulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethyl-phenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethyl-phenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl)

sulfonate; 2,2,2-trifluoro-1-(4-thiomethyl-phenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propyl-sulfonate; 2,2,2-trifluoro-1-[4-methylsulfonylphenyl]-ethanone oxime-O-propylsulfonate; 1,3-bis[l-(4-phenoxy-phenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxy-phenyl]-ethanone oxime-O-propylsulfonate; 2,2,2-trifluoro-1-[2-thiophenyl]-ethanone oxime-O-propylsulfonate; 2,2,2-trifluoro-1-[1-dioxa-thiophen-2-yl)]-ethanone oxime-O-propylsulfonate; 2,2,2-trifluoro-1-(4-(3-(4-(2,2,2-trifluoro-1-(trifluoromethanesulfonyloxyimino)-ethyl)-phenoxy)-propoxy)-phenyl)ethanone oxime (trifluoromethanesulfonate); 2,2,2-trifluoro-1-(4-(3-(4-(2,2,2-trifluoro-1-(1-propanesulfonyloxyimino)-ethyl)-phenoxy)-propoxy)-phenyl)ethanone oxime(1-propanesulfonate); and 2,2,2-trifluoro-1-(4-(3-(4-(2,2,2-trifluoro-1-(1-butane-sulfonyloxyimino)-ethyl)-phenoxy)-propoxy)-phenyl)ethanone oxime(1-butanesulfonate). Also included are the oxime sulfonates described in U.S. Pat. No. 6,916,591, for example, 2,2,2-trifluoro-1-(4-(3-(4-(2,2,2-trifluoro-1-(4-(4-methylphenylsulfonyloxy)phenylsulfonyloxyimino)-ethyl)-phenoxy)-propoxy)-phenyl)ethanone oxime(4-(4-methylphenyl-sulfonyloxy)phenylsulfonate) and 2,2,2-trifluoro-1-(4-(3-(4-(2,2,2-trifluoro-1-(2,5-bis(4-methylphenylsulfonyloxy)-benzenesulfonyloxy)phenylsulfonyloxyimino)-ethyl)-phenoxy)-propoxy)-phenyl)ethanone oxime(2,5-bis(4-methylphenyl-sulfonyloxy)benzenesulfonyloxy)phenylsulfonate). Also included are compounds of the foregoing skeleton having substituted thereon 2-benzoyloxy-1,1,3,3,3-pentafluoro-propanesulfonate, 1,1,3,3,3-pentafluoro-2-(4-phenylbenzoyl-oxy)propanesulfonate, 1,1,3,3,3-pentafluoro-2-pivaloyloxy-propanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantane-carbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane) methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are the oxime sulfonates described in JP-A 9-95479 and JP-A 9-230588 and the references cited therein, for example, α-(p-toluenesulfonyloxyimino)-phenylacetonitrile,
α-(p-chlorobenzenesulfonyloxyimino)-phenylacetonitrile,
α-(4-nitrobenzenesulfonyloxyimino)-phenylacetonitrile,
α-(4-nitro-2-trifluoromethylbenzenesulfonyloxyimino)-phenylacetonitrile,
α-(benzenesulfonyloxyimino)-4-chlorophenylacetonitrile,
α-(benzenesulfonyloxyimino)-2,4-dichlorophenylacetonitrile,
α-(benzenesulfonyloxyimino)-2,6-dichlorophenylacetonitrile,
α-(benzenesulfonyloxyimino)-4-methoxyphenylacetonitrile,
α-(2-chlorobenzenesulfonyloxyimino)-4-methoxyphenylaceto-nitrile,
α-(benzenesulfonyloxyimino)-2-thienylacetonitrile,
α-(4-dodecylbenzenesulfonyloxyimino)-phenylacetonitrile,
α-[(4-toluenesulfonyloxyimino)-4-methoxyphenyl]acetonitrile,
α-[(dodecylbenzenesulfonyloxyimino)-4-methoxyphenyl]aceto-nitrile,
α-(tosyloxyimino)-3-thienylacetonitrile,
α-(methylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile, and
α-(n-butylsulfonyloxyimino)-1-cyclohexenylacetonitrile.

Also included are compounds of the foregoing skeleton having substituted thereon
2-benzoyloxy-1,1,3,3,3-pentafluoropropanesulfonate,
1,1,3,3,3-pentafluoro-2-(4-phenylbenzoyloxy)propane-sulfonate,
1,1,3,3,3-pentafluoro-2-pivaloyloxypropanesulfonate,
2-cyclohexanecarbonyloxy-1,1,3,3,3-pentafluoropropane-sulfonate,
1,1,3,3,3-pentafluoro-2-furoyloxypropanesulfonate,
2-naphthoyloxy-1,1,3,3,3-pentafluoropropanesulfonate,
2-(4-tert-butylbenzoyloxy)-1,1,3,3,3-pentafluoropropane-sulfonate,
2-adamantanecarbonyloxy-1,1,3,3,3-pentafluoropropane-sulfonate,
2-acetyloxy-1,1,3,3,3-pentafluoropropanesulfonate,
1,1,3,3,3-pentafluoro-2-hydroxypropanesulfonate,
1,1,3,3,3-pentafluoro-2-tosyloxypropanesulfonate,
adamantanemethoxycarbonyldifluoromethanesulfonate,
1-(3-hydroxymethyladamantane)methoxycarbonyldifluoromethane-sulfonate,
methoxycarbonyldifluoromethanesulfonate,
1-(hexahydro-2-oxo-3,5-methano-2H-cyclopenta[b]furan-6-yl-oxycarbonyl)difluoromethanesulfonate, and
4-oxo-1-adamantyloxycarbonyldifluoromethanesulfonate.

Also included are oxime sulfonates having the formula:

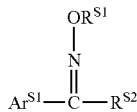

wherein $R^{s1}$ is a substituted or unsubstituted haloalkylsulfonyl or halobenzenesulfonyl group of 1 to 10 carbon atoms, $R^{s2}$ is a haloalkyl group of 1 to 11 carbon atoms, and $Ar^{s1}$ is substituted or unsubstituted aromatic or hetero-aromatic group, as described in WO 2004/074242.

Examples include 2-[2,2,3,3,4,4,5,5-octafluoro-1-(nonafluorobutylsulfonyloxyimino)-pentyl]-fluorene,
2-[2,2,3,3,4,4-pentafluoro-1-(nonafluorobutylsulfonyloxyimino)-butyl]-fluorene,
2-[2,2,3,3,4,4,5,5,6,6-decafluoro-1-(nonafluorobutylsulfonyl-oxyimino)-hexyl]-fluorene,
2-[2,2,3,3,4,4,5,5-octafluoro-1-(nonafluorobutylsulfonyloxy-imino)-pentyl]-4-biphenyl,
2-[2,2,3,3,4,4-pentafluoro-1-(nonafluorobutylsulfonyloxy-imino)-butyl]-4-biphenyl, and
2-[2,2,3,3,4,4,5,5,6,6-decafluoro-1-(nonafluorobutylsulfonyl-oxyimino)-hexyl]-4-biphenyl.

Also included are compounds of the foregoing skeleton having substituted thereon
2-benzoyloxy-1,1,3,3,3-pentafluoropropanesulfonate,
1,1,3,3,3-pentafluoro-2-(4-phenylbenzoyloxy)propane-sulfonate,
1,1,3,3,3-pentafluoro-2-pivaloyloxypropanesulfonate,
2-cyclohexanecarbonyloxy-1,1,3,3,3-pentafluoropropane-sulfonate,
1,1,3,3,3-pentafluoro-2-furoyloxypropanesulfonate,
2-naphthoyloxy-1,1,3,3,3-pentafluoropropanesulfonate,
2-(4-tert-butylbenzoyloxy)-1,1,3,3,3-pentafluoropropane-sulfonate,
2-adamantanecarbonyloxy-1,1,3,3,3-pentafluoropropane-sulfonate,
2-acetyloxy-1,1,3,3,3-pentafluoropropanesulfonate,
1,1,3,3,3-pentafluoro-2-hydroxypropanesulfonate,
1,1,3,3,3-pentafluoro-2-tosyloxypropanesulfonate,
adamantanemethoxycarbonyldifluoromethanesulfonate,
1-(3-hydroxymethyladamantane)methoxycarbonyldifluoromethane-sulfonate,
methoxycarbonyldifluoromethanesulfonate,
1-(hexahydro-2-oxo-3,5-methano-2H-cyclopenta[b]furan-6-yl-oxycarbonyl)difluoromethanesulfonate, and
4-oxo-1-adamantyloxycarbonyldifluoromethanesulfonate.

Suitable bisoxime sulfonates include those described in JP-A 9-208554, for example,
bis(α-(4-toluenesulfonyloxy)imino)-p-phenylenediacetonitrile,
bis(α-(benzenesulfonyloxy)imino)-p-phenylenediacetonitrile,
bis(α-(methanesulfonyloxy)imino)-p-phenylenediacetonitrile,
bis(α-(butanesulfonyloxy)imino)-p-phenylenediacetonitrile,
bis(α-(10-camphorsulfonyloxy)imino)-p-phenylenediaceto-nitrile,
bis(α-(4-toluenesulfonyloxy)imino)-p-phenylenediacetonitrile,
bis(α-(trifluoromethanesulfonyloxy)imino)-p-phenylenediaceto-nitrile,
bis(α-(4-methoxybenzenesulfonyloxy)imino)-p-phenylenediaceto-nitrile,
bis(α-(4-toluenesulfonyloxy)imino)-m-phenylenediacetonitrile,
bis(α-(benzenesulfonyloxy)imino)-m-phenylenediacetonitrile,
bis(α-(methanesulfonyloxy)imino)-m-phenylenediacetonitrile,
bis(α-(butanesulfonyloxy)imino)-m-phenylenediacetonitrile,
bis(α-(10-camphorsulfonyloxy)imino)-m-phenylenediaceto-nitrile,
bis(α-(4-toluenesulfonyloxy)imino)-m-phenylenediacetonitrile,
bis(α-(trifluoromethanesulfonyloxy)imino)-m-phenylenediaceto-nitrile, and
bis(α-(4-methoxybenzenesulfonyloxy)imino)-m-phenylenediaceto-nitrile. Also included are compounds of the foregoing skeleton having substituted thereon
2-benzoyloxy-1,1,3,3,3-pentafluoropropanesulfonate,
1,1,3,3,3-pentafluoro-2-(4-phenylbenzoyloxy)propane-sulfonate,
1,1,3,3,3-pentafluoro-2-pivaloyloxypropanesulfonate,
2-cyclohexanecarbonyloxy-1,1,3,3,3-pentafluoropropane-sulfonate,
1,1,3,3,3-pentafluoro-2-furoyloxypropanesulfonate,
2-naphthoyloxy-1,1,3,3,3-pentafluoropropanesulfonate,
2-(4'-tert-butylbenzoyloxy)-1,1,3,3,3-pentafluoropropane-sulfonate,
2-adamantanecarbonyloxy-1,1,3,3,3-pentafluoropropane-sulfonate,
2-acetyloxy-1,1,3,3,3-pentafluoropropanesulfonate,
1,1,3,3,3-pentafluoro-2-hydroxypropanesulfonate,
1,1,3,3,3-pentafluoro-2-tosyloxypropanesulfonate,
adamantanemethoxycarbonyldifluoromethanesulfonate,
1-(3-hydroxymethyladamantane)methoxycarbonyldifluoromethane-sulfonate,
methoxycarbonyldifluoromethanesulfonate,
1-(hexahydro-2-oxo-3,5-methano-2H-cyclopenta[b]furan-6-yl-oxycarbonyl)difluoromethanesulfonate, and
4-oxo-1-adamantyloxycarbonyldifluoromethanesulfonate.

Of these, preferred photoacid generators are sulfonium salts, bissulfonyldiazomethanes, N-sulfonyloxyimides, oxime-O-sulfonates and glyoxime derivatives. More preferred photoacid generators are sulfonium salts, bissulfonyldiazomethanes, N-sulfonyloxyimides, and oxime-O-sulfonates. Typical examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate,
triphenylsulfonium 2,4,6-triisopropylbenzenesulfonate,
4-tert-butoxyphenyldiphenylsulfonium p-toluenesulfonate,
4-tert-butoxyphenyldiphenylsulfonium camphorsulfonate,
4-tert-butoxyphenyldiphenylsulfonium 4-(4'-toluenesulfonyl-oxy)benzenesulfonate,
tris(4-methylphenyl)sulfonium camphorsulfonate,
tris(4-tert-butylphenyl)sulfonium camphorsulfonate,
4-tert-butylphenyldiphenylsulfonium camphorsulfonate,
4-tert-butylphenyldiphenylsulfonium nonafluoro-1-butanesulfonate,
4-tert-butylphenyldiphenylsulfonium pentafluoroethyl-perfluorocyclohexanesulfonate,
4-tert-butylphenyldiphenylsulfonium perfluoro-1-octanesulfonate,
triphenylsulfonium 1,1-difluoro-2-naphthylethanesulfonate,
triphenylsulfonium 1,1,2,2-tetrafluoro-2-(norbornan-2-yl)-ethanesulfonate, triphenylsulfonium 2-benzoyloxy-1,1,3,3,3-pentafluoropropanesulfonate,
triphenylsulfonium 1,1,3,3,3-pentafluoro-2-(pivaloyloxy)-propanesulfonate,
triphenylsulfonium 2-cyclohexanecarbonyloxy-1,1,3,3,3-pentafluoropropanesulfonate,
triphenylsulfonium 2-(2-naphthoyloxy)-1,1,3,3,3-pentafluoro-propanesulfonate,
triphenylsulfonium adamantanemethoxycarbonyldifluoromethane-sulfonate,
triphenylsulfonium 1-(3-hydroxymethyladamantane)methoxy-carbonyldifluoromethanesulfonate,
triphenylsulfonium methoxycarbonyldifluoromethanesulfonate,
4-tert-butylphenyldiphenylsulfonium 2-benzoyloxy-1,1,3,3,3-pentafluoropropanesulfonate,
4-tert-butylphenyldiphenylsulfonium 1,1,3,3,3-pentafluoro-2-(pivaloyloxy)propanesulfonate,
4-tert-butylphenyldiphenylsulfonium 2-cyclohexanecarbonyloxy-1,1,3,3,3-pentafluoropropanesulfonate,
4-tert-butylphenyldiphenylsulfonium 2-(2-naphthoyloxy)-1,1,3,3,3-pentafluoropropanesulfonate,
4-tert-butylphenyldiphenylsulfonium adamantanemethoxycarbonyldifluoromethanesulfonate,
4-tert-butylphenyldiphenylsulfonium 1-(3-hydroxymethyladamantane)methoxycarbonyldifluoromethanesulfonate,
4-tert-butylphenyldiphenylsulfonium methoxycarbonyldifluoro-methanesulfonate,
2-oxo-2-phenylethylthiacyclopentanium 2-benzoyloxy-1,1,3,3,3-pentafluoropropanesulfonate,
2-oxo-2-phenylethylthiacyclopentanium 2-cyclohexanecarbonyl-oxy-1,1,3,3,3-pentafluoropropanesulfonate,
triphenylsulfonium perfluoro-1,3-propylenebissulfonylimide,
triphenylsulfonium bispentafluoroethylsulfonylimide,
bis(tert-butylsulfonyl)diazomethane,
bis(cyclohexylsulfonyl)diazomethane,
bis(2,4-dimethylphenylsulfonyl)diazomethane,
bis(4-(n-hexyloxy)phenylsulfonyl)diazomethane,
bis(2-methyl-4-(n-hexyloxy)phenylsulfonyl)diazomethane,
bis(2,5-dimethyl-4-(n-hexyloxy)phenylsulfonyl)diazomethane,
bis(3,5-dimethyl-4-(n-hexyloxy)phenylsulfonyl)diazomethane,
bis(2-methyl-5-isopropyl-4-(n-hexyloxy)phenylsulfonyl)-diazomethane,
bis(4-tert-butylphenylsulfonyl)diazomethane,
N-camphorsulfonyloxy-5-norbornene-2,3-dicarboxylic acid imide,
N-p-toluenesulfonyloxy-5-norbornene-2,3-dicarboxylic acid imide,
2-[2,2,3,3,4,4,5,5-octafluoro-1-(nonafluorobutylsulfonyloxy-imino)-pentyl]-fluorene,
2-[2,2,3,3,4,4-pentafluoro-1-(nonafluorobutylsulfonyloxy-imino)-butyl]-fluorene,
2-[2,2,3,3,4,4,5,5,6,6-decafluoro-1-(nonafluorobutylsulfonyl-oxyimino)-hexyl]-fluorene,
2-[2,2,3,3,4,4,5,5-octafluoro-1-(2-(cyclohexanecarbonyloxy)-1,1,3,3,3-pentafluoropropanesulfonyloxyimino)-pentyl]-fluorene,
2-[2,2,3,3,4,4-pentafluoro-1-(2-(cyclohexanecarbonyloxy)-1,1,3,3,3-pentafluoropropanesulfonyloxyimino)-butyl]-fluorene, and
2-[2,2,3,3,4,4,5,5,6,6-decafluoro-1-(nonafluorobutylsulfonyl-oxyimino)-hexyl]-fluorene.

In the resist composition, an appropriate amount of the photoacid generator is, but not limited to, 0.1 to 10 parts, and especially 0.1 to 5 parts by weight per 100 parts by weight of the base resin. Too high a proportion of the photoacid generator may give rise to problems of degraded resolution and foreign matter upon development and resist film peeling. The photoacid generators may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid and an onium salt capable of generating a weak acid are used in admixture, an exchange from the strong acid to the weak acid as above can take place, but it never happens that the weak acid collides with the unreacted onium salt capable of generating a strong acid to induce a salt exchange. This is because of a likelihood of an onium cation forming an ion pair with a stronger acid anion.

In the resist composition, there may be added a compound which is decomposed with an acid to generate another acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

Organic Solvent

The organic solvent (C) used herein may be any organic solvent in which the base resin, acid generator, and additives are soluble. Illustrative, non-limiting, examples of the organic solvent include ketones such as cyclohexanone and methyl 2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone.

These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is about 200 to 1,000 parts, especially about 400 to 800 parts by weight per 100 parts by weight of the base resin in the resist composition.

Nitrogen-Containing Compound

In the resist composition, an organic nitrogen-containing compound or compounds may be compounded as the sensitivity regulator (D). The organic nitrogen-containing compound used herein is preferably a compound capable of suppressing the rate of diffusion when the acid generated by the photoacid generator diffuses within the resist film. The inclusion of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

The organic nitrogen-containing compound used herein may be any of well-known organic nitrogen-containing compounds which are commonly used in prior art resist compositions, especially chemically amplified resist compositions. Suitable organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, carbamate derivatives, and ammonium salts.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, truisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinolinyl derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). A typical nitrogen-containing compound having sulfonyl group is 3-pyridinesulfonic acid. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, truisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

In addition, organic nitrogen-containing compounds of the following general formula (B)-1 may also be included alone or in admixture.

$$N(X)_n(Y)_{3-n} \quad (B)\text{-}1$$

In the formula, n is equal to 1, 2 or 3; side chain Y is independently hydrogen or a straight, branched or cyclic $C_1$-$C_{20}$ alkyl group in which some or all hydrogen atoms may be replaced by fluorine atoms and which may contain an ether or hydroxyl group; and side chain X is independently selected from groups of the following general formulas (X)-1 to (X)-3, and two or three X's may bond together to form a ring.

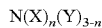  (X)-1

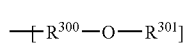  (X)-2

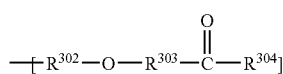  (X)-3

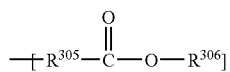

In the formulas, $R^{300}$, $R^{302}$ and $R^{305}$ are independently straight or branched $C_1$-$C_4$ alkylene groups; $R^{301}$ and $R^{304}$ are independently hydrogen, or straight, branched or cyclic $C_1$-$C_{20}$ alkyl groups in which some or all hydrogen atoms may be replaced by fluorine atoms and which may contain at least one hydroxyl, ether, ester group or lactone ring; $R^{303}$ is a single bond or a straight or branched $C_1$-$C_4$ alkylene group; and $R^{306}$ is a straight, branched or cyclic $C_1$-$C_{20}$ alkyl group in which some or all hydrogen atoms may be replaced by fluorine atoms and which may contain at least one hydroxyl, ether, ester group or lactone ring.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more organic nitrogen-containing compounds having cyclic structure represented by the following general formula (B)-2.

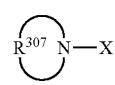  (B)-2

Herein X is as defined above, and $R^{307}$ is a straight or branched $C_2$-$C_{20}$ alkylene group in which some or all hydrogen atoms may be replaced by fluorine atoms and which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Also, one or more organic nitrogen-containing compounds having cyano group represented by the following general formulae (B)-3 to (B)-6 may be blended.

(B)-3

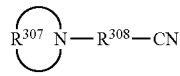

(B)-4

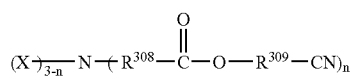

(B)-5

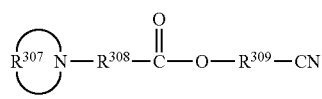

(B)-6

Herein, X, $R^{307}$ and n are as defined above, and $R^{308}$ and $R^{309}$ are each independently a straight or branched $C_1$-$C_4$ alkylene group.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiono-nitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-amino-propionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds having an imidazole structure and a polar functional group, represented by the general formula (B)-7.

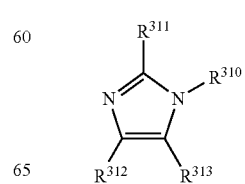

(B)-7

Herein, $R^{310}$ is a straight, branched or cyclic $C_2$-$C_{20}$ alkyl group in which some or all hydrogen atoms may be replaced by fluorine atoms and which contains at least one polar functional group selected from among hydroxyl, carbonyl, ester, ether, sulfide, carbonate, cyano and acetal groups. $R^{311}$, $R^{312}$ and $R^{313}$ are each independently a hydrogen atom, a straight, branched or cyclic $C_1$-$C_{10}$ alkyl group, aryl group or aralkyl group.

Also included are organic nitrogen-containing compounds having a benzimidazole structure and a polar functional group, represented by the general formula (B)-8.

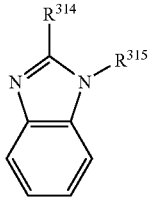
(B)-8

Herein, $R^{314}$ is a hydrogen atom, a straight, branched or cyclic $C_1$-$C_{10}$ alkyl group, aryl group or aralkyl group. $R^{315}$ is a straight, branched or cyclic $C_1$-$C_{20}$ alkyl group in which some or all hydrogen atoms may be replaced by fluorine atoms and which contains a polar functional group, with the proviso that the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

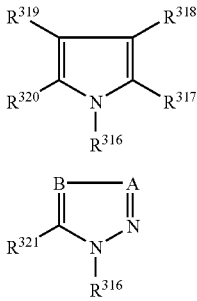
(B)-9

(B)-10

Herein, A is a nitrogen atom or $=$C—$R^{322}$, B is a nitrogen atom or $=$C—$R^{323}$, $R^{316}$ is a straight, branched or cyclic $C_2$-$C_{20}$ alkyl group in which some or all hydrogen atoms may be replaced by fluorine atoms and which contains at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic $C_1$-$C_{10}$ alkyl group or aryl group, or a pair of $R^{317}$ and $R^{318}$ and a pair of $R^{319}$ and $R^{320}$ taken together, may form a benzene, naphthalene or pyridine ring; $R^{321}$ is a hydrogen atom, a straight, branched or cyclic $C_1$-$C_{10}$ alkyl group or aryl group; $R^{322}$ and $R^{323}$ each are a hydrogen atom, a straight, branched or cyclic $C_1$-$C_{10}$ alkyl group or aryl group, or a pair of $R^{321}$ and $R^{323}$, taken together, may form a benzene or naphthalene ring.

Also included are organic nitrogen-containing compounds of aromatic carboxylic ester structure having the general formulae (B)-11 to (B)-14.

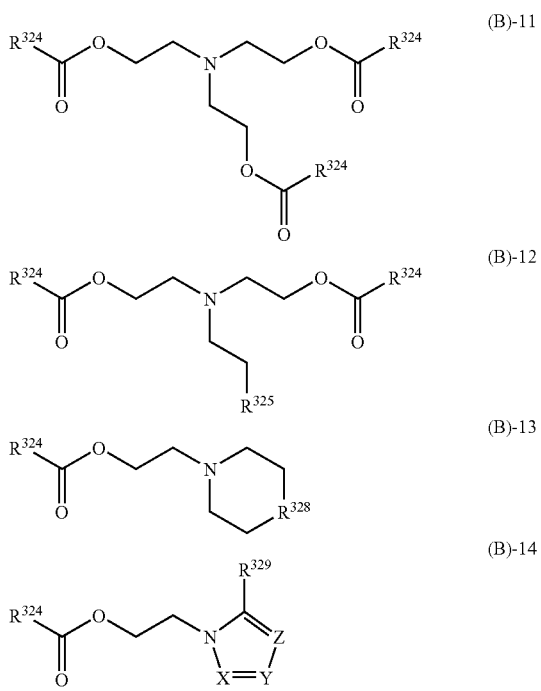

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring.

Further included are organic nitrogen-containing compounds of 7-oxanorbornane-2-carboxylic ester structure having the general formula (B)-15.

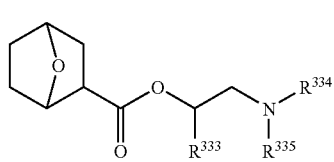
(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms.

The organic nitrogen-containing compound is preferably formulated in an amount of 0.001 to 2 parts, and especially 0.01 to 1 part by weight, per 100 parts by weight of the base resin. Less than 0.001 pbw of the nitrogen-containing compound achieves no or little addition effect whereas more than 2 parts would result in too low a sensitivity.

Surfactant

The resist composition of the invention may further comprise (E) a surfactant which is commonly used for improving the coating characteristics. The surfactant may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

To the resist composition of the invention, other components such as dissolution inhibitors, acidic compounds, stabilizers, dyes and the like may be added if necessary. Optional components may be added in conventional amounts so long as this does not compromise the objects of the invention.

Using the resist composition of the invention, patterns may be formed by any known lithographic technique. Typically, the composition is applied onto a substrate (e.g., Si, $SiO_2$, SiN, SiON, TiN, WSi, BPSG, SOG, organic antireflective coating, Cr, CrO, CrON, MoSi, etc.) for IC microfabrication by a suitable coating technique such as spin coating, roll coating, flow coating, dip coating, spray coating or doctor coating. The coating is prebaked on a hot plate at a temperature of 60 to 150° C. for about 0.1 to 10 minutes, preferably 80 to 140° C. for 0.5 to 5 minutes. The resulting resist film is generally 0.05 to 2.0 μm thick. A patterning mask having the desired pattern is placed over the resist film, and the resist film is then exposed to radiation, preferably having an exposure wavelength of up to 300 nm, such as UV, deep-UV, excimer laser light, electron beam, x-ray, γ-ray and synchrotron radiation. The exposure dose is preferably in the range of about 1 to 200 mJ/cm², more preferably about 10 to 100 mJ/cm². Light exposure may be done by a conventional exposure process or in some cases, by an immersion lithography process of providing a liquid fill, typically water, between the projection lens and the resist. In the case of immersion lithography, if necessary, a topcoat may be applied onto the resist film before exposure, which is generally know as "top coat process." The resist film is then post-exposure baked (PEB) on a hot plate at 60 to 150° C. for 0.1 to 5 minutes, and preferably at 80 to 140° C. for 0.5 to 3 minutes. Finally, development may be carried out using as the developer an aqueous alkali solution, such as 0.1 to 5 wt %, and preferably 2 to 3 wt %, tetramethylammonium hydroxide (TMAH), this being done by a conventional method such as dip, puddle, or spray technique for a period of 0.1 to 3 minutes, and preferably 0.5 to 2 minutes. These steps result in the formation of the desired pattern on the substrate. If necessary, the pattern as developed can be heat treated for adjusting the pattern size, which is generally known as "thermal flow process." Of the various types of high-energy radiation that may be used, the resist composition of the invention is best suited to micropattern formation with, in particular, deep-UV rays having a wavelength of 260 to 120 nm or excimer laser beams, extremely short UV, x-rays or electron beams.

EXAMPLE

Synthesis Examples, Examples and Comparative Examples are given below by way of illustration and not by way of limitation. The weight average molecular weight (Mw) and dispersity (Mw/Mn) of a polymer are determined by gel permeation chromatography versus polystyrene standards. All parts are by weight (pbw).

Monomer Synthesis Examples

Polymerizable acid-labile ester compounds were synthesized as follows.

Monomer Synthesis Example 1

Synthesis of [(1-methylcyclohexyl)methoxy]methyl methacrylate (Monomer 1)

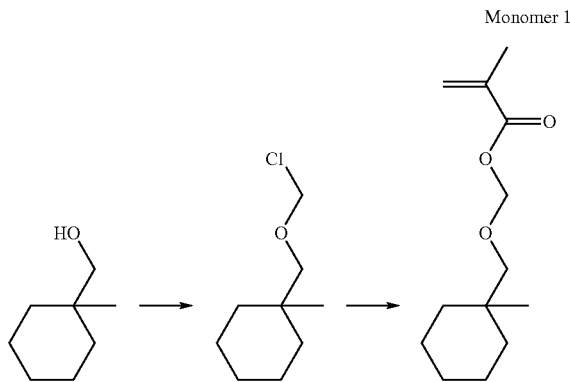

Monomer 1

Under ice cooling and stirring, hydrogen chloride was blown into a mixture of 128 g of (1-methylcyclohexyl)methanol, 400 g of hexane, and 36 g of paraformaldehyde, until the is reactant alcohol disappeared on gas chromatography analysis. The excess hydrogen chloride was purged by feeding nitrogen into the reactor, after which the water layer was removed by separatory operation. The solution was dried over magnesium sulfate and the solids filtered off, yielding a hexane solution of chloromethyl[(1-methylcyclohexyl)methyl] ether.

Under ice cooling and stirring, 116 g of triethylamine was added to a mixture of 103 g of methacrylic acid and 400 g of toluene. Subsequently, the hexane solution of chloromethyl [(1-methylcyclohexyl)methyl] ether was added dropwise to this solution. The reaction solution was stirred for 16 hours at room temperature. By an ordinary aqueous workup and solvent distillation, a crude product was obtained. It was purified by vacuum distillation, obtaining 204 g (yield 90%) of the target compound, [(1-methylcyclohexyl)-methoxy]methyl methacrylate.

Monomer Synthesis Example 2

Synthesis of [(2-methyl-2-norbornyl)methoxy]methyl methacrylate (Monomer 2)

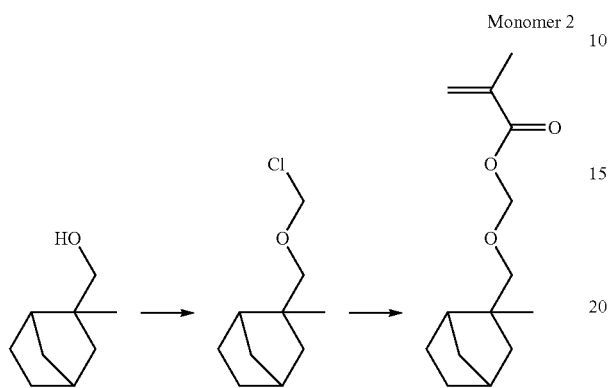

Monomer 2

Synthesis was performed by the same procedure as in Monomer Synthesis Example 1 except that an equimolar amount of (2-methyl-2-norbornyl)methanol was used instead of (1-methylcyclohexyl)methanol. There was obtained [(2-methyl-2-norbornyl)methoxy]methyl methacrylate (yield 91%).

IR (thin film) of a mixture of two stereoisomers (isomer ratio 68/32): ν=2956, 2871, 1725, 1637, 1452, 1322, 1297, 1186, 1159, 1147, 1099, 1006, 952, 916, 813 cm$^{-1}$ $^1$H-NMR (600 MHz in CDCl$_3$) of a mixture of two stereoisomers (isomer ratio 68/32): δ=0.82 (0.68H, dd), 0.86 (0.32H, dd), 0.95-1.05 [3.32H, m, inclusive of 1.01 (0.96H, s), 1.02 (2.04H, s)], 1.10-1.25 (2H, m), 1.25-1.40 (1.68H, m), 1.45-1.65 (3H, m), 1.90-2.05 (4H, m), 2.10-2.20 (1H, m), 3.25 (0.68H, d), 3.38 (0.32H, d), 3.42 (0.68H, d), 3.51 (0.32H, m), 5.34 (0.68H, d), 5.35 (0.32H, d), 5.36 (0.68H, d), 5.39 (0.32H, d), 5.55-5.65 (1H, m), 6.15-6.20 (1H, m)

Monomer Synthesis Example 3

Synthesis of [(2-methyl-2-adamantyl)methoxy]methyl methacrylate (Monomer 3)

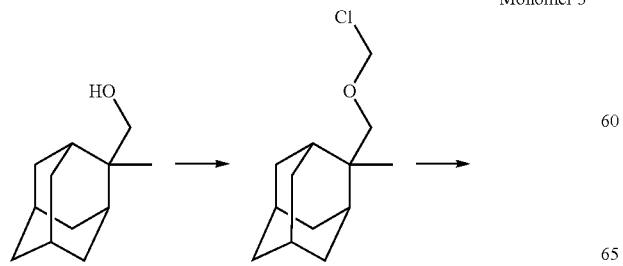

Monomer 3

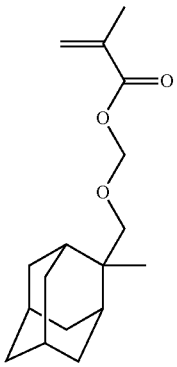

Synthesis was performed by the same procedure as in Monomer Synthesis Example 1 except that an equimolar amount of (2-methyl-2-adamantyl)methanol was used instead of (1-methylcyclohexyl)methanol. There was obtained [(2-methyl-2-adamantyl)methoxy]methyl methacrylate (yield 89%).

IR (thin film): ν=2994, 2912, 2863, 1725, 1637, 1479, 1465, 1454, 1411, 1321, 1295, 1168, 1141, 1095, 1006, 950, 914, 813 cm$^{-1}$ $^1$H-NMR (600 MHz in CDCl$_3$): δ=1.08 (3H, s), 1.50-1.55 (6H, m), 1.65 (2H, m), 1.81 (2H, m), 1.90-2.00 (5H, m), 2.03 (2H, m), 3.67 (2H, s), 5.35 (2H, s), 5.58 (1H, m), 6.14 (1H, m)

Monomer Synthesis Example 4

Synthesis of [(1R)-endo-fenchyloxy]methyl methacrylate (Monomer 4)

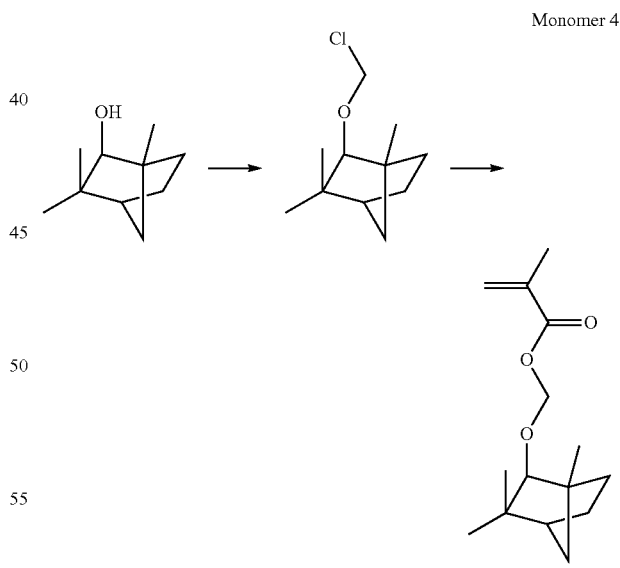

Monomer 4

Synthesis was performed by the same procedure as in Monomer Synthesis Example 1 except that an equimolar amount of (1R)-endo-fenchyl alcohol was used instead of (1-methylcyclohexyl)methanol. There was obtained [(1R)-endo-fenchyloxy]methyl methacrylate (yield 94%).

IR (thin film): ν=2956, 2929, 2873, 1724, 1639, 1459, 1452, 1411, 1375, 1322, 1297, 1153, 1097, 1006, 952, 917, 813 cm$^{-1}$ $^1$H-NMR (600 MHz in CDCl$_3$): δ=0.84 (3H, s), 0.90-1.00 (1H, m), 1.01 (3H, s), 1.06 (3H, s), 1.10 (1H, dd), 1.38 (1H, m), 1.44 (1H, m), 1.60-1.75 (3H, m), 1.95 (3H, dd), 3.20 (1H, d), 5.30 (1H, d), 5.38 (1H, d), 5.60 (1H, dq), 6.16 (1H, dq)

Monomer Synthesis Example 5

Synthesis of [(2,2,6,6-tetramethylcyclohexyloxy)methyl]methacrylate (Monomer 5)

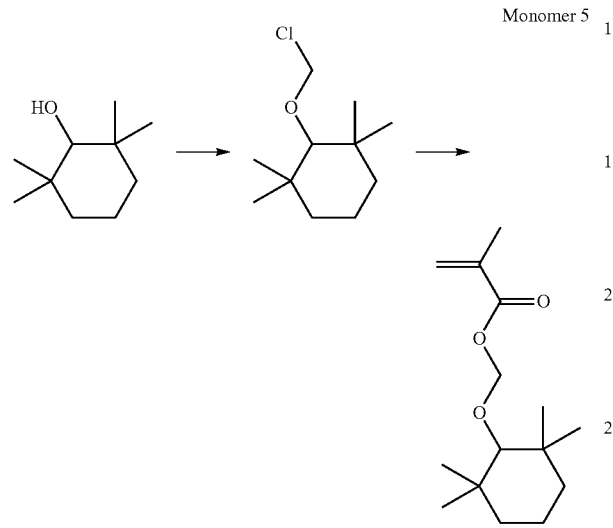

Synthesis was performed by the same procedure as in Monomer Synthesis Example 1 except that an equimolar amount of 2,2,6,6-tetramethylcyclohexanol was used instead of (1-methylcyclohexyl)methanol. There was obtained [(2,2,6,6-tetramethylcyclohexyloxy)methyl]methacrylate (yield 88%).

Monomer Synthesis Example 6

Synthesis of [(9,9-dimethyl-8-tricyclo[5.2.1.0$^{2,6}$]decyl-oxy)methyl]methacrylate (Monomer 6)

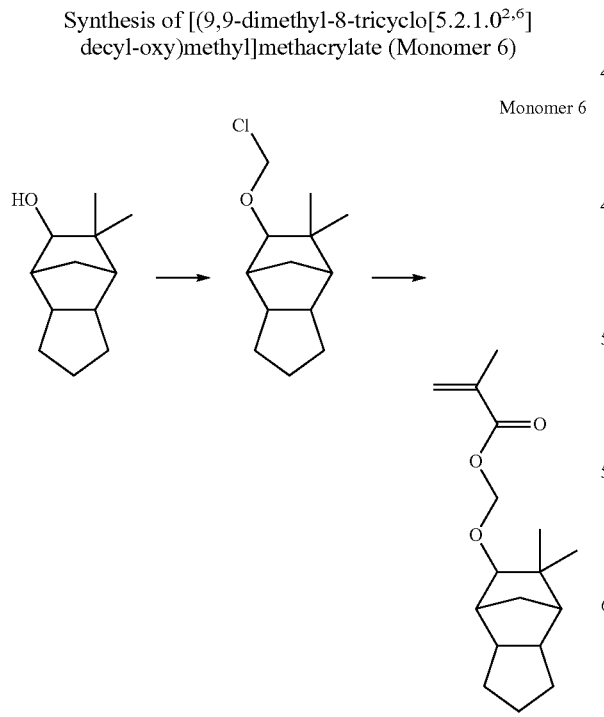

Synthesis was performed by the same procedure as in Monomer Synthesis Example 1 except that an equimolar amount of 9,9-dimethyl-8-tricyclo[5.2.1.0$^{2,6}$]decanol was used instead of (1-methylcyclohexyl)methanol. There was obtained [(9,9-dimethyl-8-tricyclo[5.2.1.0$^{2,6}$]decyloxy)methyl]methacrylate (yield 86%).

Monomer Synthesis Example 7

Synthesis of [(9-bicyclo[3.3.1]nonyloxy)methoxy]methyl methacrylate (Monomer 7)

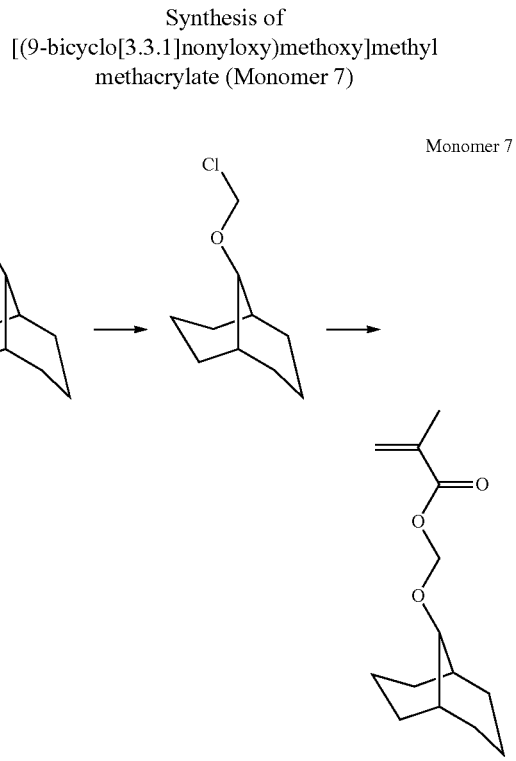

Synthesis was performed by the same procedure as in Monomer Synthesis Example 1 except that an equimolar amount of 9-bicyclo[3.3.1]nonanol was used instead of (1-methylcyclohexyl)methanol. There was obtained [(9-bicyclo[3.3.1]nonyloxy)methoxy]methyl methacrylate (yield 92%).

Monomer Synthesis Example 8

Synthesis of [(1-methylcyclohexyl)methoxy]methyl acrylate (Monomer 8)

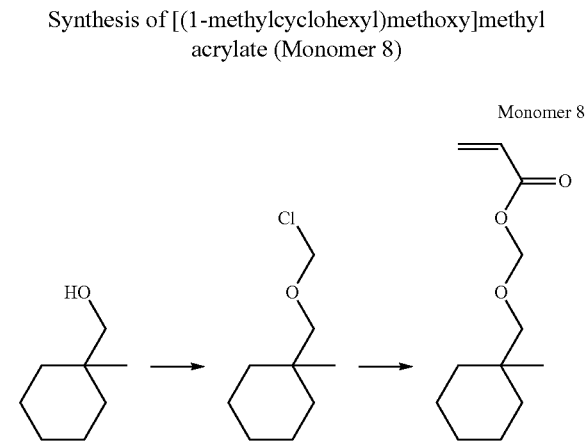

Synthesis was performed by the same procedure as in Monomer Synthesis Example 1 except that an equimolar amount of acrylic acid was used instead of methacrylic acid. There was obtained [(1-methylcyclohexyl)methoxy]methyl acrylate (yield 81%).

Monomer Synthesis Example 9

Synthesis of [(1-methylcyclohexyl)methoxy]methyl α-trifluoromethylacrylate (Monomer 9)

Monomer 9

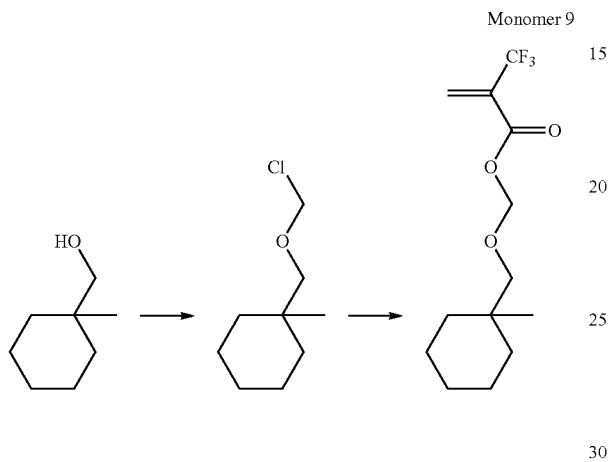

Synthesis was performed by the same procedure as in Monomer Synthesis Example 1 except that an equimolar amount of α-trifluoromethylacrylic acid was used instead of methacrylic acid. There was obtained [(1-methylcyclohexyl)-methoxy]methyl α-trifluoromethylacrylate (yield 73%).

Monomer Synthesis Example 10

Synthesis of [(1-methylcyclohexyl)methoxy]methyl 5-norbornene-2-carboxylate (Monomer 10)

Monomer 10

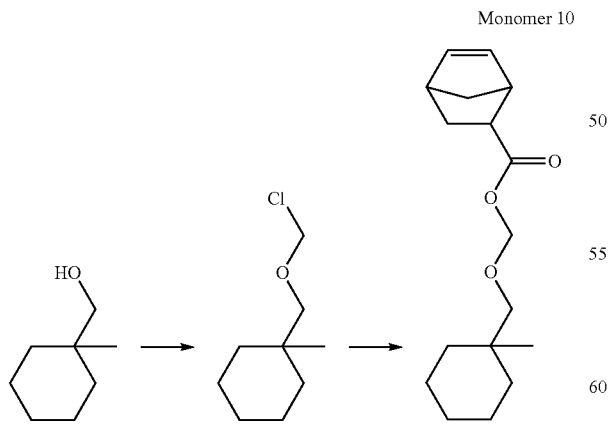

Synthesis was performed by the same procedure as in Monomer Synthesis Example 1 except that an equimolar amount of 5-norbornene-2-carboxylic acid was used instead of methacrylic acid. There was obtained [(1-methylcyclohexyl)-methoxy]methyl 5-norbornene-2-carboxylate (yield 92%).

Polymer Synthesis Examples

Polymers were synthesized in accordance with the following formulation.

Polymer Synthesis Example 1

Synthesis of Polymer 1

Polymer 1

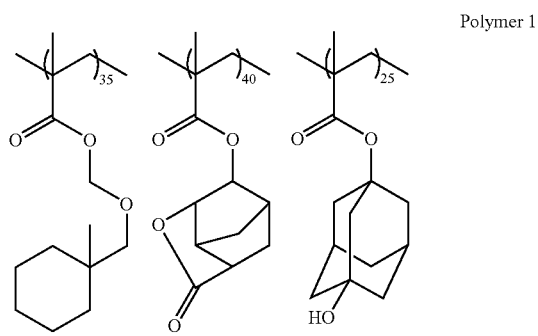

With stirring, 30.0 g of 2-butanone was heated at 80° C., to which a mixture of 13.9 g of [(1-methylcyclohexyl)-methoxy]methyl methacrylate, 10.4 g of 3-hydroxy-1-adamantyl methacrylate, 15.7 g of 3-oxo-2-oxatricyclo[4.2.1.0$^{4,8}$] nonan-9-yl methacrylate, 1.75 g of dimethyl 2,2-azobis(2-methyl-propionate) and 60.0 g of 2-butanone was added dropwise over 4 hours. The mixture was allowed to react for a further 2 hours. The reaction solution was added dropwise to 400 g of hexane, with stirring. The precipitate thus formed was filtered, washed with hexane, and dried under reduced pressure at 50° C. for 18 hours, obtaining 32.4 g (yield 81%) of the target polymer, Polymer 1.

Mw=9,200
Mw/Mn=2.10

Polymer Synthesis Examples 2 to 6

Synthesis of Polymers 2 to 6

Polymers 2 to 6 were synthesized by the same procedure as in Polymer Synthesis Example 1.

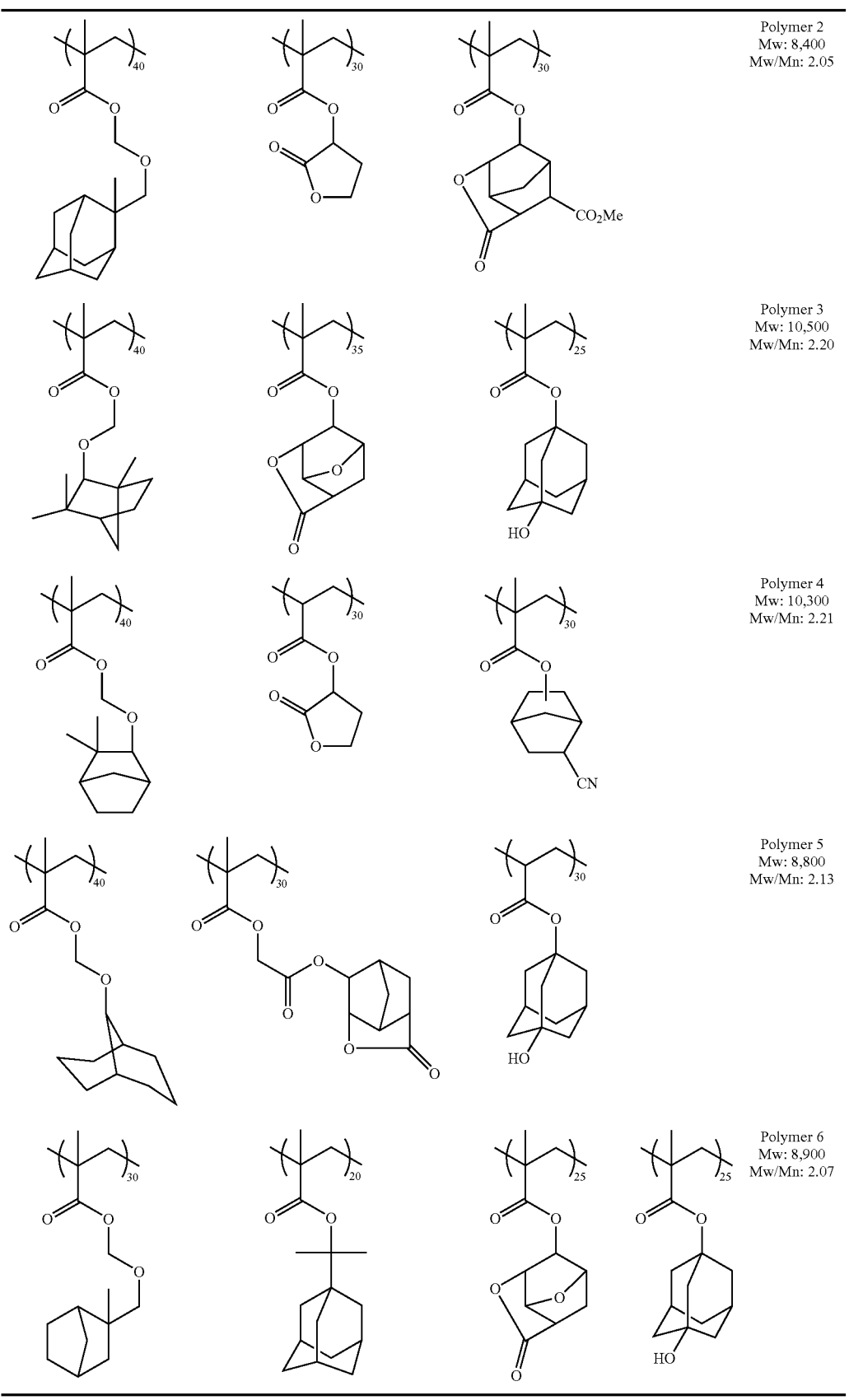

Comparative Polymer Synthesis Examples 1 to 3

Synthesis of Polymers 7 to 9

Polymers 7 to 9 were synthesized by the same procedure as in Polymer Synthesis Example 1.

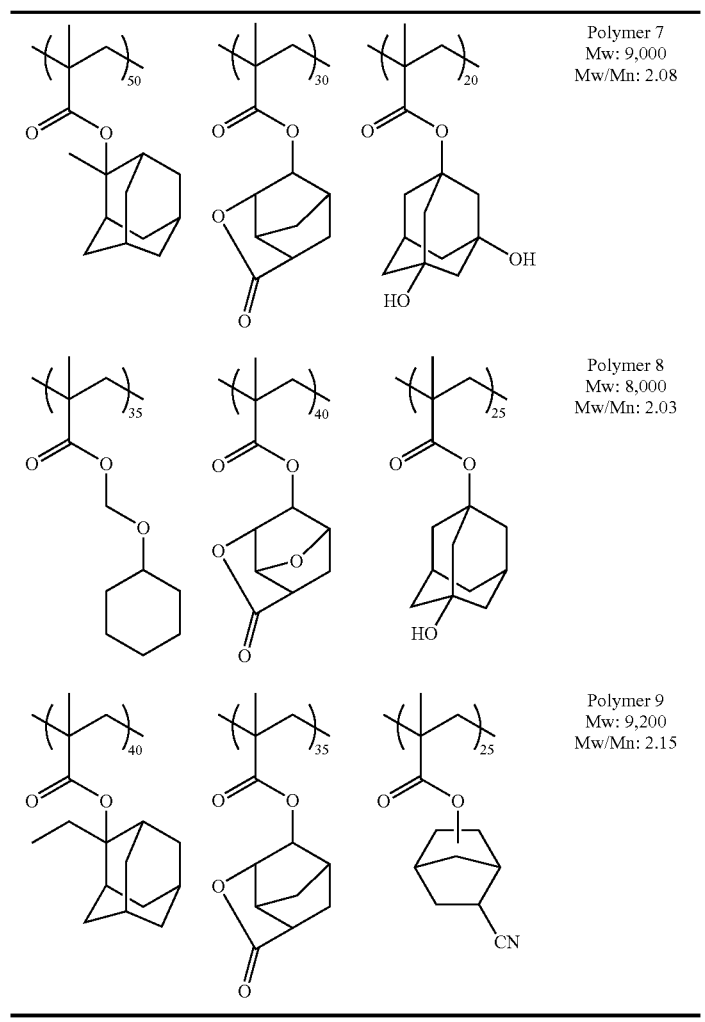

Examples and Comparative Examples

Preparation of chemically amplified resist compositions and Pattern formation

Example 1

A resist composition was prepared by dissolving the polymer of Polymer Synthesis Example 1 (Polymer 1), a photoacid generator (PAG), and a sensitivity regulator in a solvent in accordance with the formulation shown below and filtering through a Teflon@ filter with a pore diameter of 0.2 μm.

| Formulation | |
|---|---|
| (A) Base resin: | 80 pbw of Polymer 1 |
| (B) PAG: | 4.4 pbw of triphenylsulfonium nonafluorobutanesulfonate |

| -continued | |
|---|---|
| Formulation | |
| (C) Solvent: | a mixture of 560 pbw of propylene glycol monomethyl ether acetate and 240 pbw of cyclohexanone |
| (D) Sensitivity regulator: | 0.53 pbw of Amine 1 |

Amine 1

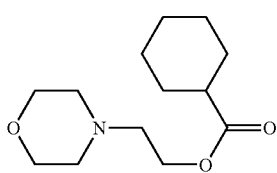

The solvent contained 0.01% by weight of surfactant KH-20 (Asahi Glass Co., Ltd.).

On a silicon wafer having an antireflective coating (ARC29A, Nissan Chemical Industries Ltd.) of 78 nm thick, the resist solution was spin coated and baked at 110° C. for 60 seconds to give a resist film having a thickness of 170 nm. Using an ArF excimer laser stepper NSR-S307E (Nikon Corp., NA 0.85, ¾ annular illumination, 6% halftone phase shift mask), the resist film was exposed. It was then baked (PEB) at 115° C. for 60 seconds, cooled to 23° C., and puddle developed at 23° C. for 30 seconds with a 2.38 wt % aqueous solution of tetramethylammonium hydroxide, forming a line-and-space pattern.

Examples 2 to 6 and Comparative Examples 1 to 3

Resist compositions were prepared according to Example 1 aside from using 80 pbw of each of Polymers 2 to 6 of Polymer Synthesis Examples 2 to 6 and Polymers 7 to 9 of Comparative Synthesis Examples. Patterns were similarly formed. The PEB step used an optimum temperature for a particular resist composition.

Tests (1) Evaluation of Resolution

The wafers as developed were observed under a top-down scanning electron microscope (TDSEM). The optimum exposure was an exposure dose (mJ/cm$^2$) which provided a resolution to a 90-nm 1:1 grouped line-and-space pattern. The maximum resolution of the resist was the minimum size (in increments of 5 nm) of the lines and spaces that were resolved and separated at the optimum exposure and reported as an index of resolution, with smaller values indicating better resolution.

(2) Evaluation of Proximity Bias

The wafers as developed were observed under a TDSEM. The optimum exposure was an exposure dose (mJ/cm$^2$) which provided a resolution to a 1:1 grouped line-and-space pattern having a line width of 90 nm. The width of an isolated line in a 1:10 line-and-space pattern having the same line width at the optimum exposure was measured. The difference in line width between isolated and grouped patterns is reported as proximity bias (or I/G bias), with smaller differences being better.

The resist compositions of Examples 1 to 6 and Comparative Examples 1 to 3 were examined for resolution and proximity bias.

Tables 1 and 2 tabulate the maximum resolution of a 1:1 line-and-space pattern and the proximity bias between 1:1 and 1:10 line-and-space patterns.

TABLE 1

| Example | Base polymer | PEB temp. (° C.) | Maximum resolution (nm) | Proximity bias (nm) |
| --- | --- | --- | --- | --- |
| 1 | Polymer-1 | 115 | 70 | 42 |
| 2 | Polymer-2 | 100 | 70 | 38 |
| 3 | Polymer-3 | 115 | 70 | 45 |
| 4 | Polymer-4 | 100 | 70 | 41 |
| 5 | Polymer-5 | 115 | 70 | 39 |
| 6 | Polymer-6 | 115 | 70 | 37 |

TABLE 2

| Comparative Example | Base polymer | PEB temp. (° C.) | Maximum resolution (nm) | Proximity bias (nm) |
| --- | --- | --- | --- | --- |
| 1 | Polymer-7 | 120 | 75 | 51 |
| 2 | Polymer-8 | 110 | 80 | 55 |
| 3 | Polymer-9 | 100 | 75 | 50 |

It is evident from Tables 1 and 2 that the resist compositions within the scope of the invention meet both a high resolution and improved proximity bias when processed by ArF excimer laser lithography.

Japanese Patent Application No. 2006-186297 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymerizable acid-labile ester compound having a structure that undergoes no acid-induced decomposition by beta-elimination and is represented by the following general formula (5):

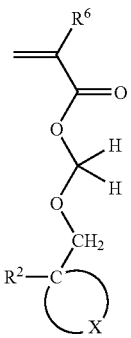

(5)

wherein $R^2$ is a straight, branched or cyclic $C_1$-$C_{10}$ alkyl group, $R^6$ is hydrogen, methyl or trifluoromethyl, and X is a straight, branched or cyclic $C_2$-$C_{20}$ alkylene group which forms an aliphatic hydrocarbon ring with the carbon atom to which it is attached at both ends, with the proviso that $R^2$ and X are free of heteroatoms other than carbon and hydrogen atoms.

2. A polymer comprising at least recurring units derived from a polymerizable acid-labile ester compound having a structure that undergoes no acid-induced decomposition by beta-elimination, and represented by formula (5):

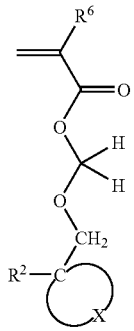

(5)

wherein $R^2$ is a straight, branched or cyclic $C_1$-$C_{10}$ alkyl group, $R^6$ is hydrogen, methyl or trifluoromethyl, and X is a straight, branched or cyclic $C_2$-$C_{20}$ alkylene group which forms an aliphatic hydrocarbon ring with the carbon atom to which it is attached at both ends, with the proviso that $R^2$ and X are free of heteroatoms other than carbon and hydrogen atoms, and having a weight average molecular weight of 2,000 to 100,000.

3. The polymer of claim 2, further comprising recurring units of at least one type selected from the following general formula (R1):

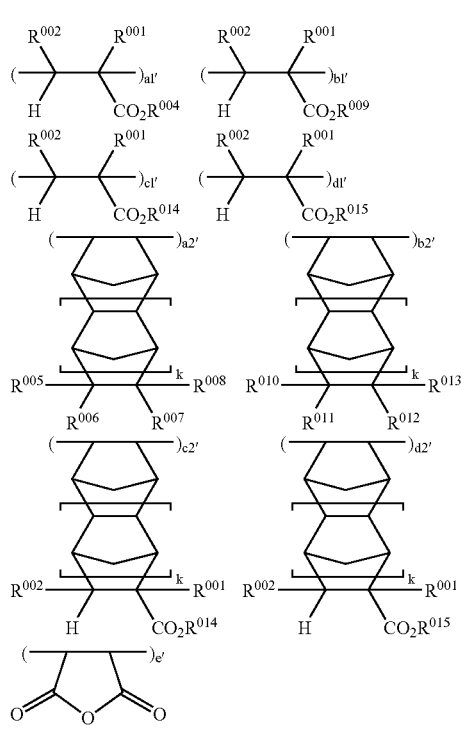

(R1)

wherein $R^{001}$ is hydrogen, fluorine, methyl, trifluoromethyl or $CH_2CO_2R^{003}$; $R^{002}$ is hydrogen, methyl or $CO_2R^{003}$; $R^{003}$ is a straight, branched or cyclic $C_1$-$C_{15}$ alkyl $R^{004}$ is hydrogen or a monovalent hydrocarbon group of 1 to 15 carbon atoms having at least one group selected from among fluorinated substituent groups, carboxyl, hydroxyl and cyano groups; at least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups, or a combination of $R^{005}$ to $R^{008}$ may bond together to form a ring, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to are each independently single bonds, hydrogen atoms or straight, branched or cyclic $C_1$-$C_{15}$ alkyl groups; $R^{009}$ is a monovalent hydrocarbon group of 3 to 15 carbon atoms containing a partial structure; at least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups, or a combination of $R^{010}$ to $R^{013}$ may bond together to form a ring, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups; $R^{014}$ is a polycyclic hydrocarbon group having 7 to 15 carbon atoms or an alkyl group containing such a polycyclic hydrocarbon group; $R^{015}$ is an acid labile group; a1', a2', b1', b2', c1', c2', d1', d2', and e' indicative of ratios of corresponding recurring units to the total recurring units in the polymer are numbers from 0 to less than 1; and k is 0 or 1.

4. The polymer of claim 2, comprising recurring units derived from the polymerizable acid-labile ester compound of formula (5) in a molar fraction of 5% to 70%.

5. A resist composition comprising the polymer of claim 2.

6. A process for forming a pattern, comprising the steps of applying the resist composition of claim 5 onto a substrate to form a resist coating; heat treating the coating and exposing to high-energy radiation or electron beam through a photomask; and heat treating the exposed coating and developing with a developer.

7. A resist composition comprising (A) the polymer of claim 2, (B) an acid generator, and (C) an organic solvent.

8. A resist composition comprising (A) the polymer of claim 2, (B) an acid generator, (C) an organic solvent, and (D) a sensitivity regulator.

9. A resist composition comprising (A) the polymer of claim 2, (B) an acid generator, (C) an organic solvent, (D) a sensitivity regulator, and (E) a surfactant.

* * * * *